United States Patent
Koiwa

Patent Number: 5,533,411
Date of Patent: Jul. 9, 1996

[54] METHOD AND APPARATUS FOR NONDESTRUCTIVE TESTING OF PHYSICAL CHARACTERISTICS OF A SPECIMEN USING ULTRASONIC WAVES

[75] Inventor: Masaichi Koiwa, Katsuta, Japan

[73] Assignee: Hitachi Construction Machinery Co., Ltd., Tokyo, Japan

[21] Appl. No.: 196,181
[22] PCT Filed: Apr. 28, 1993
[86] PCT No.: PCT/JP93/00554
§ 371 Date: Feb. 23, 1994
§ 102(e) Date: Feb. 23, 1994
[87] PCT Pub. No.: WO94/00755
PCT Pub. Date: Jan. 6, 1994

[30] Foreign Application Priority Data

Jun. 25, 1992 [JP] Japan ................ 4-191698
Jun. 29, 1992 [JP] Japan ................ 4-194834
Jun. 30, 1992 [JP] Japan ................ 4-196323

[51] Int. Cl.⁶ .................. G01N 29/08; G01N 29/18
[52] U.S. Cl. .......................... 73/598; 73/602
[58] Field of Search ............ 73/602, 597, 598, 73/627, 629

[56] References Cited

U.S. PATENT DOCUMENTS

| | | | |
|---|---|---|---|
| 3,603,136 | 9/1971 | Diamond et al. | 73/597 |
| 3,774,444 | 11/1973 | Kent | 73/597 |
| 3,844,163 | 10/1974 | Di Leo | 73/597 |
| 3,848,460 | 11/1974 | Bantz et al. | 73/597 |
| 4,114,455 | 9/1978 | Walker | 73/597 |
| 4,386,527 | 6/1983 | Maucher | 73/597 |

FOREIGN PATENT DOCUMENTS

| | | |
|---|---|---|
| 4130908 | 3/1992 | Germany. |
| 2165050 | 4/1986 | United Kingdom. |
| WO88/01054 | 2/1988 | WIPO. |

Primary Examiner—Hezron E. Williams
Assistant Examiner—Rose M. Finley
Attorney, Agent, or Firm—Fay, Sharpe, Beall, Fagan, Minnich & McKee

[57] ABSTRACT

The sound velocity (V) in a cast specimen is measured with ultrasonic wave and the sound velocity ratio (V/Vm) between the sound velocity in said specimen and the sound velocity (Vm) in a specified metal corresponding to said specimen is attained; by converting this sound velocity ratio to a physical quantity to be determined (e.g., percent spheroidicity of graphite, state classification, tensile strength or percent elongation) in accordance with an empirical formula (530) or the like which relate to the sound velocity ratio, a physical characteristic value related to said specimen is computed. As a result, values of analysis on the state of castings structure and their characteristic values can be measured or computed with high probability in a nondestructive and convenient manner.

31 Claims, 18 Drawing Sheets

| NAME | GREY CAST IRON | CV CAST IRON | | SPHEROIDAL GRAPHITE CAST IRON |
|---|---|---|---|---|
| | | CV CAST IRON | | |
| MORPHOLOGY OF GRAPHITE GRAINS | FLAKY | VERMICULAR | | SPHEROIDAL |
| |  |  | |  |

Fig. 18

| MORPHOLOGY OF GRAPHITE GRAINS | CAST IRON PRODUCTS ||||||
|---|---|---|---|---|---|---|
| NAME | GRAY CAST IRON || CV CAST IRON || SPHEROIDAL GRAPHITE CAST IRON ||
| MORPHOLOGY OF GRAPHITE GRAINS | FLAKY || VERMICULAR || SPHEROIDAL ||
| TYPE AND SYMBOL | TYPE | SYMBOL | TYPE | SYMBOL | TYPE | SYMBOL |
| | 1 | FC 100 | YET TO BE SPECIFIED IN JIS | YET TO BE SPECIFIED IN JIS (FCV) | 0 | FCD370 |
| | 2 | FC 150 | | | 1 | FCD400 |
| | 3 | FC 200 | | | 2 | FCD450 |
| | 4 | FC 250 | | | 3 | FCD500 |
| | 5 | FC 300 | | | 4 | FCD600 |
| | 6 | FC 350 | | | 5 | FCD700 |
| | — | — | | | 6 | FCD800 |

സ്റ്റ്5,533,411

METHOD AND APPARATUS FOR NONDESTRUCTIVE TESTING OF PHYSICAL CHARACTERISTICS OF A SPECIMEN USING ULTRASONIC WAVES

TECHNICAL FIELD

This invention relates to a method and an apparatus for ultrasonic measurement. More particularly, this invention relates to a method by which the values of physical characteristics such as tensile strength, percent elongation, and the percent spheroidicity of graphite, as well as the values of state analysis, can be measured or calculated on castings such as gray cast iron, CV cast iron, and spheroidal graphite cast iron by ultrasonic waves in a nondestructive manner. The invention also relates to an apparatus for implementing the method for ultrasonic measurement.

BACKGROUND ART

Both the manufacturer and the user of a machine part generally have serious concerns as to whether that part is truly made of a material to specifications. This is because the use of an incorrect or defective material has high potential to lead directly to a disastrous accident due to failure of the part.

Therefore, the manufacturer makes it a rule to conduct materials tests on each of the parts produced, and guarantees the authenticity of an individual part by issuing a materials test performance list which certifies that it has been produced from the material to specifications. In the case of cast iron products, the materials tests to be conducted include a tensile test and a hardness test. As for spheroidal graphite iron products, an additional test is conducted to determine the percent spheroidicity of graphite.

While this is generally the basic way adopted to certify the authenticity of materials, materials tests require about three or four days including the processing of test pieces and other steps, so the manufacturer has desired the development of a method that enables various materials characteristics to be estimated in a simpler and quicker way.

On the side of the user, a need exists for verifying on the actual sample that the part of interest is truly made of the material to specifications. However, to prepare a test piece for materials testing, the actual sample must be broken, and it has been desired to develop a method by which tensile strength and other properties can satisfactorily be estimated in a nondestructive manner.

As for the test to estimate the percent spheroidicity of graphite in spheroidal cast irons to be evaluated by various materials tests, an apparatus for ultrasonic measurement was developed in the early eighties that was capable of indirect determination of the percent spheroidicity of graphite using the fact that the velocity of sound (the term "sound velocity" as used herein means the speed of propagation of ultrasonic waves) varied with the shape of graphite particles.

A block diagram of an apparatus that measures the sound velocity on a cast specimen by ultrasonic wave and which computes automatically the percent spheroidicity of graphite in the specimen is shown in FIG. 16.

In the drawing, numeral 1 designates an ultrasonic probe, 2 is an ultrasonic flaw detector, 3 is a D/A converter circuit, 4 is a bus line, 5 is a ROM, 6 is a RAM, 7 is a keyboard (KBD), 8 is a CRT, and 9 is a microprocessor (MPU).

Details of interface circuits and the like that are connected between these components are omitted from FIG. 16.

Further referring to FIG. 16, numeral 51 designates a program for measuring the sound velocity, 52 is a program for computing the percent spheroidicity, 53$p$ is a V-S conversion formula, and 54$p$ is a main program; these programs are stored in ROM 5 and executed by MPU 9 to perform the functions they are assigned respectively.

Sound velocity measuring program 51 is activated by main program 54$p$ when it is instructed to start measurement via keyboard 7, and the ultrasonic flaw detector 2 is controlled via bus line 4 to measure the sound velocity on the specimen 1$a$. Stated more specifically, the ultrasonic wave sent from the ultrasonic probe 1 is partly reflected by the surface of the specimen 1$a$, whereas the remainder propagates through the interior of the specimen 1$a$ and is also reflected by its bottom. These reflected waves are detected with the ultrasonic probe 1 and upon receiving the detection signal, the ultrasonic flaw detector 2 measures the time from the point of detection of the surface reflected wave to the point of detection of the bottom reflected wave. The measured time is sent to the D/A converter circuit 3 and thence delivered to MPU 9 as a digital value. The delivered time is the time taken by the ultrasonic wave to go back and forth through the specimen 1$a$ and, hence, the input digital value is divided by twice the thickness of the specimen 1$a$ that is preliminarily measured and which has already been entered from the keyboard 7 and, as a result of this operation, the sound velocity on the specimen 1$a$ is determined.

The thus-measured value of sound velocity is stored in area V in RAM 6 by means of the sound velocity measuring program 51.

The program 52 for computing the percent spheroidicity is subsequently activated by the main program 54$p$ and performs a conversion process in accordance with the V-S conversion formula 53$p$, thereby computing the percent spheroidicity of graphite from the value of sound velocity stored in area V. The computed percent spheroidicity of graphite is stored in area S in RAM 6.

The V-S conversion formula 53$p$ represents the relationship between the sound velocity and the percent spheroidicity of graphite for castings, and is an empirically determined conversion formula. Stated specifically, this is a regression line as constructed by plotting the results of measurement on a plurality of castings in relevant positions on a coordinate system, the horizontal axis of which may typically represent the sound velocity (V) as determined by ultrasonic measurement while the vertical axis represents the percent spheroidicity of graphite (S) as determined by direct means of measurement in accordance with the JIS (Japanese Industrial Standards) (see 53$a$ in FIG. 17).

The percent spheroidicity of graphite stored in area S which has been computed on the basis of this empirical formula is displayed on CRT 8 by the main program 54$p$ as the result of measurement.

The tensile strength of castings is measured directly by a so-called "tensile test", or a test in which the load or the like that is applied when a test piece worked to a prescribed shape breaks is measured on a calibrated tensile tester.

However, the tensile test takes time in preparing test pieces, working them, conducting the test, etc. and, hence, three or four days are necessary before the inspector knows the acceptability of the material being tested. Under the circumstances, there has been a need for a method by which the tensile strength of a cast product can be known as soon as it is produced, and which enables one to be sure that the cast product has been definitely yielded from the material to specifications.

The tensile strength of a cast product depends on the tensile strength of its base and the shape of fine graphite grains that are distributed in the base and, hence, the tensile strength of the cast product would be estimated by combining its hardness, which is a substitute value of the tensile strength of the base, with the percent spheroidicity of graphite which indicates the shape of graphite. On the basis of this idea, a method has been proposed that determines indirectly the tensile strength of the cast product from the value of sound velocity and hardness.

FIG. 20 is a block diagram showing an apparatus for implementing this indirect method, namely, an apparatus for ultrasonic measurement that measures the sound velocity on a cast specimen by ultrasonic wave and which computes automatically the tensile strength of the specimen from the measured value of sound velocity and the value of hardness as measured in a separate step. In FIG. 20, the constituent elements that are the same as those which are shown in FIG. 16 are identified by like numerals.

In the drawing, numeral 53 refers to a classification program, 54 is a tensile strength computing program, and 55 is a main program, all of these programs being new.

These programs are stored in ROM 5 and executed by MPU 9 to perform the functions they are assigned respectively.

The operation of the apparatus shown in FIG. 20 is described below without going into details of the part of the operation that has already been explained in connection with the case shown in FIG. 16. First, the sound velocity on the specimen 1a is measured and stored in area V in RAM 6. Then, the percent spheroidicity of graphite is computed from the stored value of sound velocity in area V in accordance with the empirical V-S conversion formula, and then stored in area S in RAM 6. Stated specifically, this V-S conversion formula is a regression line as is constructed by plotting the results of measurement on a plurality of castings in relevant positions on a coordinate system, the horizontal axis of which may typically represent the sound velocity (V) as determined by ultrasonic measurement while the vertical axis represents the percent spheroidicity of graphite (S) as determined by direct means of measurement in accordance with the JIS (see 53a in FIG. 17).

When the percent spheroidicity of graphite (S) is determined, the classification program 53 is activated by the main program 55. Then, the state of castings structure is classified by the classification program 53 in accordance with the value of the percent spheroidicity of graphite (S), and a value indicating the specific type, such as gray cast iron (FC), CV graphite cast iron (FCV), or spheroidal graphite cast iron (FCD), is written into area (F). For the sake of reference, the classification according to the JIS specifications is shown in FIG. 18.

In the next step, the Brinell hardness of the specimen 1a as measured with a separate hardness tester is entered via the keyboard 7 and stored in area HB. Then, the tensile strength computing program 54 is activated by the main program 55. In accordance with the formula for conversion from the product of sound velocity and hardness to tensile strength, the program 54 computes the tensile strength from the product of sound velocity (V) and Brinell hardness (HB) that have been measured on the specimen 1a. The computed tensile strength is stored in area σB' in RAM 6.

It should be noted here that the above-mentioned formula for conversion to tensile strength consists of three expressions that are selectively used depending upon the state of castings structure: conversion expression 54a for FCD, conversion expression 54b for FCV, and conversion expression 54c for FC. Stated specifically, these expressions are regression lines as constructed by plotting the results of direct measurement on a plurality of castings in relevant positions on a coordinate system, the horizontal axis of which represents the product of sound velocity and hardness (V×HB) while the vertical axis represents the tensile strength (σB) (see 54a, 54b, and 54c in FIG. 19).

The thusly determined tensile strength (σB') and the like are displayed on CRT 8 by the main program 55 as the result of measurement.

In the case of spheroidal graphite cast iron and CV graphite cast iron, it is also necessary to know their percent elongation as a characteristic value for verifying that they are made of the material to specifications.

The percent elongation of castings has heretofore been measured by a method that depends on a tensile test as conducted using test pieces having a prescribed specification geometry.

However, no convenient and indirect substitute method has ever been developed. As already mentioned, the material species of cast iron can be specified by the materials characteristic values that are attained by materials tests including a tensile test and the like; among them, the percent spheroidicity of graphite and the tensile strength have been the subject of reviews on proposed alternatives that rely upon the technique of measuring the sound velocity. However, sound velocity measurement using an apparatus for ultrasonic measurement involves variations in the result of measurement due to the apparatus such as those in the characteristics of the ultrasonic probe, the ultrasonic flaw detector and D/A conversion. Further, one cannot neglect the variations in the result of measurement due to the inspector such as those in the measurement of thickness of the specimen and in adjustments like the setting of the gate to the ultrasonic flaw detector.

Under these circumstances, the empirical formula on the percent spheroidicity of graphite that has been attained by a certain apparatus and inspector for ultrasonic measurement (see 53a in FIG. 14) does not necessarily agree with the empirical formula that has been attained by another apparatus and inspector for ultrasonic measurement (see 53b in FIG. 15). The sound velocity that should correspond to a cast product having 70% spheroidicity of graphite is 5.56 km/s in one case but it is 5.62 km/s in the other case, and the two values differ considerably. What is more, such differences occur frequently. Therefore, in spite of the nondestructive and convenient nature of the measurement, the result is not reliable and this causes problems.

Next, the specific problems as regards the measurement of the percent spheroidicity of graphite will be further discussed. In the conventional method and apparatus for ultrasonic measurement, an approximate value of percent spheroidicity of graphite is computed from the sound velocity in accordance with an available empirical formula. By means of this indirect technique, the state of castings structure is analyzed in a nondestructive manner.

However, the relationship between the sound velocity and the percent spheroidicity of graphite is such that one does not correlate well to the other (see FIG. 17). Hence, an approximate value of the percent spheroidicity of graphite that has been attained by the empirical formula at issue or the result of analysis on the state of castings structure contains such large errors that they are by no means suitable for practical use as substitutes for the true percent spheroidicity of graphite.

Under the circumstances, inspections such as nondestructive delivery or acceptance inspection of cast products and the like that have damage have only low reliability in the results or inspection and, even if certain troubles occur in the production process, one may often overlook the adverse effects of such troubles by failing to detect them.

Similar problems occur in connection with the measurement of tensile strength on castings. A plurality of formulae exist for conversion to tensile strength (see FIG. 19) which are derived on the basis of the results of measurement on the typical states of casting structures that belong to the respective types. Since no general-purpose expression, relation, or the like that unifies them has yet been established, these formulae are selectively used in accordance with the specific type of casting. Under the circumstances, a cast product of an intermediate state that is not typical is dealt with by different conversion formulae depending upon the type in which the cast product is classified, and this causes great variations in the computed result of measurement; hence, the conversion formulae under consideration are by no means suitable for practical use as means of warranting the product and the like.

There are also problems in connection with the measurement of percent elongation on castings. These are drawbacks including the following: In the state of the art, the only method that can be adopted is by conducting a tensile test and, since this involves a destructive measurement, not all products in the production lot can be inspected; since the geometry of test pieces is prescribed by specifications, several days of time and cost are taken in preparation for the measurement; and, since a dedicated tensile test apparatus is necessary, no inspectors other than testing organizations and the like which have suitable apparatus are able to conduct the measurement unless they ask for help by an outsider.

An object, therefore, of the present invention is to solve these problems of the prior art by realizing a method and apparatus for ultrasonic measurement on castings by which the values of state analysis and characteristic values (e.g. the percent spheroidicity of graphite, state classification, tensile strength, and percent elongation) of cast specimens can be measured or computed with high probability in a nondestructive and convenient manner.

DISCLOSURE OF INVENTION

This object of the present invention can be attained by a method of ultrasonic measurement on castings, a first aspect of which is that the sound velocity in a east specimen is measured and a physical characteristic value of the specimen that has a physical correlation with the sound velocity is determined. According to the method, the sound velocity ratio between the sound velocity in the specimen and the sound velocity in a given metal that corresponds to the specimen (hereafter, the "sound velocity ratio") is attained, and this sound velocity ratio is converted to the physical quantity of interest according to an empirical formula associated with the sound velocity ratio or a means of conversion based on the result of measurement, thereby determining the physical characteristic value of the specimen.

The above-mentioned object of the present invention can also be attained according to the invention by an apparatus for ultrasonic measurement on castings, a first aspect of which measures the sound velocity in a cast specimen and measures a physical characteristic value of the specimen that has a physical correlation with the sound velocity. More particularly, the apparatus employs an empirical formula by which a first physical quantity is processed to determine a second physical quantity that is equivalent to the physical characteristic value or a means of conversion by which the first physical quantity is converted to the second quantity which is equivalent to the physical characteristic value. A reference sound velocity generating means generates a reference sound velocity by ultrasonic measurement on a steel product. Additionally, a characteristic value generating means determines the physical quantity by the empirical formula or means of conversion, and generates the thus-determined physical quantity as the physical characteristic value, the sound velocity ratio between the sound velocity in the specimen as attained by ultrasonic measurement on the specimen and the reference sound velocity being considered an equivalent of the first physical quantity.

Further, the invention defines the quantity as the sound velocity ratio between the sound velocity in a certain cast product (specimen) and the sound velocity in the steel product, the two velocities being attained by measurement with the same apparatus ultrasonic measurement, and the second physical quantity as the physical characteristic value that is measured on the certain cast product and which is measured directly with a measuring apparatus other than the ultrasonic measurement. The empirical formula or means of conversion possesses either a characteristic function, a table, or a processing procedure that represents the correlation between the first physical quantity and the second physical quantity which have been measured on a plurality of samples of the certain cast product.

In the first aspects of the method and apparatus for ultrasonic measurement according to this invention which relates to the measurement to a physical characteristic of castings, the empirical formula and the like are specified on the basis of the relationship between a characteristic value of a cast product with respect to the sound velocity ratio between a steel product and the cast product. Since variations in the value of measurement which depend on the apparatus or inspector are likely (more specifically, even the sound velocities as measured on a cast product and a steel product by means of the same apparatus or the like have variations of the same tendency), if the ratio between the measured values is taken, the corresponding variations will cancel each other. Hence, the sound velocity ratio between a steel product and a cast product is hardly affected by the influences due to variations in the apparatus and the like.

Consequently, the empirical formula and the like that are based on the correlation between the sound velocity ratio and the characteristic value have a wide range of applications and are even effective for other apparatus or the like that are different from that which has been used in determining the empirical formula and the like.

Further, the method and apparatus of the present invention for ultrasonic measurement of a physical characteristic of castings have the advantage that when measuring or computing a characteristic value of a cast specimen, the sound velocity in a steel product is measured separately, or a previously measured value of sound velocity for the steel product is entered separately, as input data and, on the basis of the measured sound velocity in the specimen, the sound velocity ratio between the specimen and the steel product is computed. In this case, too, the sound velocity ratio is substantially free from variations since it is determined by the same apparatus and the like.

Stated more specifically, the empirical formula and the like, which are based on the relationship between a characteristic value as determined by a direct method for the measurement of the characteristic value and the sound velocity ratio, are free from variations and have a wide range of applications in that they can be used with any type of apparatus for ultrasonic measurement. Then, once the empirical formula and the like are attained, measurements that involve destruction are not necessary. Further, when measuring a physical characteristic of a cast product as an actual product, the sound velocity in the cast product is normalized by the sound velocity in the steel product to yield the sound velocity ratio and, in accordance with the empirical formula of interest, a physical characteristic value of the cast product is computed from the sound velocity ratio. In this way, the effect of variations due to the apparatus and the inspector can be eliminated.

Therefore, the physical characteristic value is computed from the variation-free sound velocity ratio in accordance with the general-purpose formula. As a result, the effect due to similarities or dissimilarities in the apparatus for ultrasonic measurement or the inspector is reduced to the extent that the physical characteristic value as associated with the cast specimen can be ultrasonically measured or computed with high probability in a nondestructive and convenient manner.

The above-mentioned object of the present invention can also be attained by the method of ultrasonic measurement, a second aspect of which comprises a method of measuring the sound velocity in a cast specimen and analyzing the state of casting structure of the specimen that has a physical correlation with the sound velocity, characterized in that the percent carbon content of the specimen and the sound velocity in the specimen are attained. Then, in accordance with an empirical formula or a means of conversion based on the result of measurement, by which an analytical value equivalent to the state of casting structure is attained from the percent carbon content and sound velocity in a certain cast product, the analytical value corresponding to the percent carbon content and sound velocity in the specimen is attained, whereby the state of casting structure in the specimen is analyzed in terms of the analytical value.

The above-mentioned object of the present invention can also be attained by the apparatus for ultrasonic measurement, a second aspect of which comprises structure which measures the sound velocity in a cast specimen with a known percent carbon content and analyzes the state of casting structure in the specimen, characterized in that the apparatus employs an empirical formula by which a first physical quantity and a second physical quantity are processed to determine a third physical quantity that is equivalent to the state of casting structure, or a means of conversion by which a first physical quantity and a second physical quantity as two elements are converted to a third physical quantity that is equivalent to the state of casting structure; and a state evaluating means which determines the third physical quantity by the empirical formula or the means of conversion, provided that the sound velocity in the specimen as attained by ultrasonic measurement on the specimen is dealt with as or considered to be an equivalent of the first physical quantity, and that the percent carbon content is dealt with as an equivalent of the second physical quantity, the means evaluating the state of casting structure in accordance with the thusly determined third physical quantity.

Further, the first physical quantity is the sound velocity in a certain cast product according to the invention, the second physical quantity is the percent carbon content of the certain cast product, the third physical quantity is the state of casting structure that is measured on the certain cast product and which is measured directly with a measuring apparatus other than the ultrasonic measurement apparatus, and the empirical formula or means of conversion possesses either a characteristic function, a table, or a processing procedure that represents the correlation between the first physical quantity, the second physical quantity, and the third physical quantity which have been measured on a plurality of samples of the certain cast product.

The above-stated object of the present invention can also be attained by the apparatus for ultrasonic measurement, a third aspect of which comprises structure which measures the sound velocity in a cast specimen with a known percent carbon content and analyzes the state of casting structure in the specimen, characterized in that the apparatus employs an empirical formula by which a first physical quantity and a second physical quantity are processed to determine a third physical quantity that is equivalent to the state of casting structure, or a means of conversion by which a first physical quantity and a second physical quantity are converted to a third physical quantity that is equivalent to the state of casting structure; a reference sound velocity generating means generates the sound velocity, as attained by ultrasonic measurement on a steel product, as a reference sound velocity; and a state evaluating means determines the third physical quantity by the empirical formula or the means of conversion, provided that the sound velocity ratio, measured between the sound velocity in the specimen as attained by ultrasonic measurement on the specimen and the reference sound velocity, is dealt with as the first physical quantity, and provided that the percent carbon content is dealt with as an equivalent of the second physical quantity, the means evaluating the state of casting structure in accordance with the thusly determined third physical quantity.

The third aspect of the apparatus is further characterized in that the first physical quantity is the sound velocity ratio between a certain cast product and the steel product as attained by measurement with the same apparatus for ultrasonic measurement, in that the second physical quantity is the percent carbon content of the certain cast product, in that the third physical quantity is the state of casting structure that is measured on the certain cast product and which is measured directly with a measuring apparatus other than the one for ultrasonic measurement, and in that the empirical formula or means of conversion possesses either a characteristic function, a table, or a processing procedure that represents the correlation between the first physical quantity, the second physical quantity, and the third physical quantity, which have been measured on a plurality of samples of the certain cast product.

Thus, the second aspect of the method of ultrasonic measurement according to the present invention, as well as the second and third aspects of the apparatus for ultrasonic measurement, analyze the state of casting structure with a view to performing classification or the like, particularly on castings, by ultrasonic measurement, and the analysis is performed on the basis of both the present carbon content and the sound velocity or sound velocity ratio (which are hereunder abbreviated as the "sound velocity or the like"). To this end, the state of casting structure as it relates to the percent carbon content and the sound velocity or the like is measured by a direct means or the like, and the formula or means of conversion that represent the relationship between those factors is specified experimentally. By thusly performing state classification based not only on the sound velocity or the like but also on the percent carbon content, it is now possible to clearly classify the state of casting structure which has heretofore been difficult to classify, and in particular, the state of casting structure as regards the morphology of graphite or the like.

Then, in accordance with the list or the like which has been determined by the direct method of measurement, the state of casting structure of the specimen is evaluated on the basis of the sound velocity or the like that has been determined by ultrasonic measurement and its percent carbon content. Thus, a close analysis is performed on the basis of not only the sound velocity or the like but also the percent carbon content and, therefore, in spite of its indirect nature, the analysis permits the state of casting structure to be estimated more closely and more correctly than has heretofore been possible.

Consequently, the state of casting structure that is associated with the cast specimen can be measured or analyzed with high probability by ultrasonic measurement in a nondestructive and convenient manner.

The above-stated object of the present invention can also be attained by the method of ultrasonic measurement, a third aspect of which comprises ultrasonic measurement in which the sound velocity in a cast specimen is measured and the tensile strength of the specimen is determined, characterized in that the percent content and the hardness of the specimen, as well as the sound velocity in the specimen, are attained and that, in accordance with an empirical formula or a means of conversion based on the result of measurement, by which the tensile strength is attained from the percent carbon content and the hardness of a certain cast product and the sound velocity in the cast product, the tensile strength of the specimen is determined from the percent carbon content and the hardness of the specimen and the sound velocity in the specimen.

The above-stated object of the present invention can also be attained by the apparatus for ultrasonic measurement, a fourth aspect of which comprises structure which measures the sound velocity in a cast specimen with a known percent carbon content and measures the tensile strength of the specimen, characterized in that the apparatus employs an empirical formula by which a first physical quantity, a second physical quantity, and a third physical quantity are processed to determine a fourth physical quantity that is equivalent to the tensile strength, or a means of conversion by which a first physical quantity, a second physical quantity, and a third physical quantity as three elements are converted to a fourth physical quantity that is equivalent to the tensile strength; and a tensile strength computing means determines the fourth physical quantity by the empirical formula or the means of conversion, provided that the sound velocity in the specimen, as attained by ultrasonic measurement on the specimen, is dealt with as an equivalent of the first physical quantity, the percent carbon content as an equivalent of the second physical quantity, and the hardness of the specimen as an equivalent of the third physical quantity, the means outputting the thusly determined fourth physical quantity as the value of the tensile strength.

The fourth aspect is further characterized in that the first physical quantity is the sound velocity in a certain cast product, in that the second physical quantity is the percent carbon content of the certain cast product, in that the third physical quantity is the hardness of the certain cast product, in that the fourth physical quantity is the tensile strength as measured on the certain cast product by a direct means of tensile strength measurement other than the apparatus for ultrasonic measurement, and in that the empirical formula or the means of conversion possesses either a characteristic function, a table, or a processing procedure that represents the correlation between the first physical quantity, the second physical quantity, the third physical quantity, and the fourth physical quantity which have been measured on a plurality of samples of the certain cast product.

The above-stated object of the present invention can also be attained by the apparatus for ultrasonic measurement, a fifth aspect of which comprises structure which measures the sound velocity in a cast specimen with a known percent carbon content and measures the tensile strength of the specimen, characterized in that the apparatus employs an empirical formula by which a first physical quantity, a second physical quantity, and a third physical quantity are processed to determine a fourth physical quantity that is equivalent to the tensile strength, or a means of conversion by which a first physical quantity, a second physical quantity, and a third physical quantity as three elements are converted to a fourth physical quantity that is equivalent to the tensile strength; a reference sound velocity generating means by which the sound velocity as attained by ultrasonic measurement on a steel product is generated as a reference sound velocity; and a tensile strength computing means which determines the fourth physical quantity by the empirical formula or conversion means, provided that the sound velocity ratio between the sound velocity in the specimen and the reference sound velocity is dealt with as an equivalent of the first physical quantity, the percent carbon content as an equivalent of the second physical quantity, and the hardness of the specimen as an equivalent of the third physical quantity, the means outputting the thusly determined fourth physical quantity as the value of the tensile strength.

The fifth aspect is further characterized in that the first physical quantity is the sound velocity ratio between the sound velocity in a certain cast product and the sound velocity in the steel product, the two velocities being attained by measurement with the same apparatus for ultrasonic measurement; in that the second physical quantity is the percent carbon content of the certain cast product; in that the third physical quantity is the hardness of the certain cast product; in that the fourth physical quantity is the tensile strength as measured on the certain cast product by a direct means of tensile strength measurement other than the apparatus for ultrasonic measurement; and in that the empirical formula or conversion means possesses either a characteristic function, a table, or a processing procedure that represents the correlation between the first physical quantity, the second physical quantity, the third physical quantity, and the fourth physical quantity which have been measured on a plurality of samples of the certain cast product.

Thus, the third aspect of the method of ultrasonic measurement according to the present invention, as well as the fourth and fifth aspects of the apparatus for ultrasonic measurement, computes the tensile strength, particularly on castings, by ultrasonic measurement, and the computation of tensile strength is performed on the basis of the percent carbon content, the hardness, and the sound velocity or sound velocity ratio. To perform this computation or the like, the tensile strength of the cast product of interest as it relates to the percent carbon content, the hardness, and the sound velocity or the like is measured by a direct means or the like, and the formula or means of conversion that represents the relationship between those factors is specified preliminarily on an experimental basis.

By thusly establishing correlation to the tensile strength based not only on the sound velocity and hardness but also on the percent carbon content, the overlap between data of measurement of tensile strength will be limited not only for castings in a typical state but also for castings in an intermediate state and, as a result, the data to be measured can be clearly correlated to the data to be computed. In accordance with the empirical formula or the like under consideration, the tensile strength of the cast specimen is computed from the percent carbon content and the hardness of the specimen, as well as the sound velocity or the like in the specimen. By so doing, the analysis, even though an indirect method, permits the tensile strength of the cast product to be estimated in a closer and more correct way than has heretofore been possible.

Consequently, the tensile strength of the cast specimen, which is one of its characteristic values, can be measured or computed with high probability by means of ultrasonic measurement in a nondestructive and convenient manner.

The above-stated object of the present invention can also be attained by the method of ultrasonic measurement, a fourth aspect of which comprises steps in which the sound velocity in a cast specimen is measured and the percent elongation of the specimen is determined, characterized in that the percent carbon content and the hardness of the specimen, as well as the sound velocity in the specimen, are attained and that, in accordance with an empirical formula or a means of conversion based on the result of measurement, by which the percent elongation is attained from the percent carbon content and the hardness of a certain cast product and the sound velocity in the product, the percent elongation of the specimen is determined from the percent carbon content and the hardness of the specimen and the sound velocity in the specimen.

The above-stated object of the present invention can also be attained by the apparatus for ultrasonic measurement, a sixth aspect of which comprises structure which measures the sound velocity in a cast specimen with a known percent carbon content and measures the percent elongation of the specimen, characterized in that the apparatus employs an empirical formula by which a first physical quantity, a second physical quantity, and a third physical quantity are processed to determine a fourth physical quantity that is equivalent to the percent elongation, or a means of conversion by which a first physical quantity, a second physical quantity, and a third physical quantity as three elements are converted to a fourth physical quantity that is equivalent to the percent elongation; and a percent elongation computing means which determines the fourth physical quantity by the empirical formula or conversion means, provided that the sound velocity in the specimen as attained by ultrasonic measurement on the specimen is dealt with as an equivalent of the first physical quantity, the percent carbon content as an equivalent of the second physical quantity, and the hardness of the specimen as an equivalent of the third physical quantity, the means outputting the thusly determined fourth physical quantity as the value of the percent elongation.

The sixth aspect is further characterized in that the first physical quantity is the sound velocity in a certain cast product; in that the second physical quantity is the percent carbon content of the certain cast product; in that the third physical quantity is the hardness of the certain cast product; in that the fourth physical quantity is the percent elongation as measured on the certain cast product by a direct means of percent elongation measurement other than the apparatus for ultrasonic measurement; and in that the empirical formula or conversion means possesses either a characteristic function, a table, or a processing procedure that represents the correlation between the first physical quantity, the second physical quantity, the third physical quantity, and the fourth physical quantity which have been measured on a plurality of samples of the certain cast product.

The above-stated object of the present invention can also be attained by the apparatus for ultrasonic measurement, a seventh aspect of which comprises structure which measures the sound velocity in a cast specimen with a known percent carbon content and measures the percent elongation of the specimen, characterized in that the apparatus employs an empirical formula by which a first physical quantity, a second physical quantity, and a third physical quantity are processed to determine a fourth physical quantity that is equivalent to the percent elongation, or a means of conversion by which a first physical quantity, a second physical quantity, and a third physical quantity as three elements are converted to a fourth physical quantity that is equivalent to the percent elongation; a reference sound velocity generating means by which the sound velocity as attained by ultrasonic measurement on a steel product is generated as a reference sound velocity; and a percent elongation computing means which determines the fourth physical quantity by the empirical formula or conversion means, provided that the sound velocity ratio between the sound velocity in the specimen as attained by ultrasonic measurement on the specimen and the reference sound velocity is dealt with as an equivalent of the first physical quantity, the percent carbon content as an equivalent of the second physical quantity, and the hardness of the specimen as an equivalent of the third physical quantity, the means outputting the thusly determined fourth physical quantity as the value of the percent elongation.

The seventh aspect is further characterized in that the first physical quantity is the sound velocity ratio between the sound velocity in a certain cast product and the sound velocity in the steel product, the two velocities being attained by measurement with the same apparatus for ultrasonic measurement; in that the second physical quantity is the percent carbon content of the certain cast product; in that the third physical quantity is the hardness of the certain cast product; in that the fourth physical quantity is the percent elongation as measured on the certain cast product by a direct means of percent elongation measurement other than the apparatus for ultrasonic measurement; and in that the empirical formula or conversion means possesses either a characteristic function, a table, or a processing procedure that represents the correlation between the first physical quantity, the second physical quantity, the third physical quantity, and the fourth physical quantity which have been measured on a plurality of samples of the certain cast product.

The above-stated object of the present invention can also be attained by the method of ultrasonic measurement, a fifth aspect of which comprises steps in which the sound velocity in a cast specimen is measured and the percent elongation of the specimen is determined, characterized in that the specimen is a copper-containing cast iron, that the percent copper content, the percent carbon content, and the hardness of the specimen, as well as the sound velocity in the specimen are attained and that, in accordance with a function, a table, or some other means of conversion for attaining the percent elongation from the percent copper content, and the hardness of a certain cast product and the sound velocity in the product, the percent elongation of the specimen is determined from the percent copper content, the percent carbon content, and the hardness of the specimen and the sound velocity in the specimen.

The above-stated object of the present invention can also be attained by the apparatus for ultrasonic measurement, an eighth aspect of which comprises structure which measures the sound velocity in a specimen formed of a copper-containing cast iron with known percent copper and carbon contents, and measures the percent elongation of the specimen, characterized in that the apparatus employs an empirical formula by which a first physical quantity, a second physical quantity, a third physical quantity, and a fourth physical quantity are processed to determine a fifth physical quantity that is equivalent to the percent elongation, or a means of conversion by which a first physical quantity, a second physical quantity, a third physical quantity, and a fourth physical quantity as four elements are converted to a fifth physical quantity that is equivalent to the percent elongation; and a percent elongation computing means which determines the fifth physical quantity by the empirical formula or conversion means, provided that the sound velocity in the specimen as attained by ultrasonic measurement on the specimen is dealt with as an equivalent of the first physical quantity, the percent carbon content as an equivalent of the second physical quantity, the hardness of the specimen as an equivalent of the third physical quantity, and the percent copper content as an equivalent of the fourth physical quantity, the means outputting the thusly determined fifth physical quantity as the value of the percent elongation.

The fifth aspect is further characterized in that the first physical quantity is the sound velocity in a certain copper-containing cast iron; in that the second physical quantity is the percent carbon content of the certain copper-containing cast iron; in that the third physical quantity is the hardness of the certain copper-containing cast iron; in that the fourth physical quantity is the percent copper content of the certain copper-containing cast iron; in that the fifth physical quantity is the percent elongation as measured on the certain copper-containing cast iron by a direct means of percent elongation measurement other than the apparatus for ultrasonic measurement; and in that the empirical formula or conversion means possesses either a characteristic function, a table, or a processing procedure that represents the correlation between the first physical quantity, the second physical quantity, the third physical quantity, the fourth physical quantity, and the fifth physical quantity which have been measured on a plurality of samples of the certain copper-containing cast iron.

The above-stated object of the present invention can also be attained by the apparatus for ultrasonic measurement, a ninth aspect of which comprises an apparatus for ultrasonic measurement which measures the sound velocity in a specimen formed of a copper-containing cast iron with known percent copper and carbon contents and measures the percent elongation of the specimen, characterized in that the apparatus employs an empirical formula by which a first physical quantity, a second physical quantity, a third physical quantity, and a fourth physical quantity are processed to determine a fifth physical quantity that is equivalent to the percent elongation, or a means of conversion by which a first physical quantity, a second physical quantity, a third physical quantity, and a fourth physical quantity as four elements are converted to a fifth physical quantity that is equivalent to the percent elongation; a reference sound velocity generating means by which the sound velocity as attained by ultrasonic measurement on a steel product is generated as a reference sound velocity; and a percent elongation computing means which determines the fifth physical quantity by the empirical formula or conversion means, provided that the sound velocity ratio between the sound velocity in the specimen as attained by ultrasonic measurement on the specimen and the reference sound velocity is dealt with as an equivalent of the first physical quantity, the percent carbon content as an equivalent of the second physical quantity, the hardness of the specimen as an equivalent of the third physical quantity, and the percent copper content as an equivalent of the fourth physical quantity, the means outputting the thusly determined fifth physical quantity as the value of the percent elongation.

The ninth aspect is further characterized in that the first physical quantity is the sound velocity ratio between the sound velocity in a certain copper-containing cast iron and the sound velocity in the steel product, the two velocities being attained by measurement with the same apparatus for ultrasonic measurement; in that the second physical quantity is the percent carbon content of the certain copper-containing cast iron; in that the third physical quantity is the hardness of the certain copper-containing cast iron; in that the fourth physical quantity is the percent copper content of the certain copper-containing cast iron; in that the fifth physical quantity is the percent elongation as measured on the certain copper-containing cast iron by a direct means of percent elongation measurement other than the apparatus for ultrasonic measurement; and in that the empirical formula or conversion means possesses either a characteristic function, a table, or a processing procedure that represents the correlation between the first physical quantity, the second physical quantity, the third physical quantity, the fourth physical quantity, and the fifth physical quantity which have been measured on a plurality of samples of the certain copper-containing cast iron.

Thus, the fourth and fifth aspects of the method of ultrasonic measurement according to the present invention, as well as the sixth, seventh, eighth, and ninth aspects of the apparatus for ultrasonic measurement, compute the percent elongation, particularly on castings, by ultrasonic measurement, and the computation of the percent elongation of castings is performed on the basis of the percent carbon content, the hardness, and the sound velocity or sound velocity ratio (or a combination of these with the percent copper content). To perform this computation or the like, the percent elongation of the cast product of interest as it relates to the percent carbon content, the hardness, and the sound velocity or the like (or a combination of these with the percent copper content) is measured by a direct means or the like, and the formula or means of conversion that represents the relationship between these factors is specified preliminarily on an experimental basis.

By thusly establishing correlation to the percent elongation based not only on the sound velocity and hardness but also on the percent carbon content (or a combination of these with the percent copper content), the data to be measured can be clearly correlated to the data to be computed although these data have not heretofore been correlated to each other. In accordance with the empirical formula or the like under consideration, the percent elongation of the cast specimen is computed from the percent carbon content and the hardness of the specimen, and the sound velocity or the like in the specimen (or a combination of these with the percent copper content) and, by so doing, the percent elongation of the cast product can be estimated. In other words, the percent elongation of castings can be measured indirectly although this has heretofore been impossible.

Consequently, the percent elongation of the cast specimen, which is one of its characteristic values, can be measured or computed with high probability by means of ultrasonic measurement in a nondestructive and convenient manner.

If, in addition to the percent carbon content, the percent copper content is also included as a parameter, there is achieved a particular advantage in that, even in the case where the cast product to be analyzed is a copper-containing cast iron, its percent elongation can be measured in a nondestructive and convenient manner.

It should be noted here that as regards all of the above-described aspects of the method and apparatus for ultrasonic measurement, the percent carbon content may be replaced by the carbon equivalent.

It should also be noted that while the above-described empirical formula or means of conversion possesses a characteristic function, a table, or a processing procedure, the concept of this characteristic function or table embraces various items such as diagrams, graphic charts, lists, approximations, and so-called sequences, maps, tables, etc. that are related to computer programs; further, the concept of the processing procedure embraces means of conversion such as a computing procedure, a mathematical operation, a process, address tables, etc. that use or modify such a processing procedure.

The percent carbon content (or its combination with the percent copper content) which is held to be necessary for the present invention is familiar to the manufacturer who presets the proportions of components in the casting material, but usually the customer who accepts the cast product is also in the position to be knowledgeable of that factor as one of the conditions for placement of an order; therefore, aside from the special case where a cast product of unknown origin has to be analyzed for research and experimental purposes, the factor under consideration will be no impediment to practical implementation of the present invention. Measurement of the hardness of the specimen also causes no inconvenience since this can be performed with a hardness meter that is simple to operate.

BRIEF DESCRIPTION OF DRAWINGS

FIG. 18 is a chart illustrating the morphology and classification of graphite types in castings;

BEST MODE FOR CARRYING OUT THE INVENTION

Figure 1:
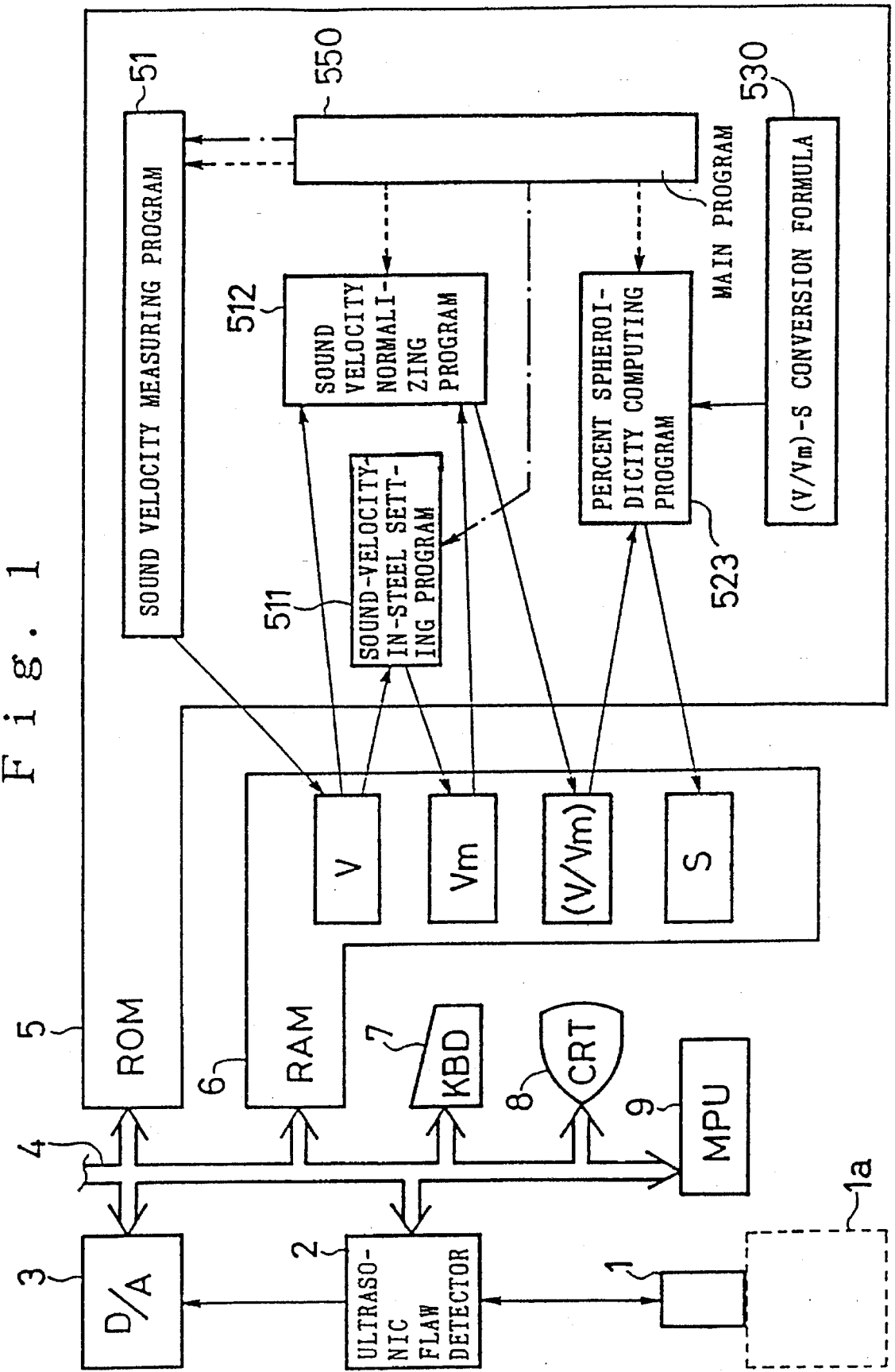
FIG. 1 is a block diagram showing a first example of the apparatus for ultrasonic measurement which features the constitution of the present invention, and which computes automatically the percent spheroidicity of graphite as one of the physical characteristic values of a cast product.

A first example of the present invention is described below in detail with reference to the drawings. FIG. 1 is a block diagram showing an apparatus for implementing the method of the present invention for ultrasonic measurement of a physical characteristic of castings, namely, an apparatus for ultrasonic measurement that measures the sound velocity in a cast specimen by ultrasonic energy, and which computes automatically the percent spheroidicity of graphite in the specimen.

In the diagram, numeral 1 designates an ultrasonic probe, 2 an ultrasonic flaw detector, 3 a D/A converter circuit, 4 a bus line, 5 a ROM, 6 a RAM, 7 a keyboard (KBD), 8 a CRT, and 9 a microprocessor (MPU). Details of interface circuits and the like that are connected between these components are omitted from FIG. 1.

Further referring to FIG. 1, numeral 51 designates a program for measuring the sound velocity, 511 is a program for setting the sound velocity in steel, 512 is a program for normalizing the sound velocity, 523 is a program for computing the percent spheroidicity, 530 is a (V/Vm)–S conversion formula, and 550 is a main program; these programs are stored in ROM 5 and executed by MPU 9 to perform the functions respectively assigned to them.

It should be noted that ultrasonic probe 1 through microprocessor 9 and sound velocity measuring program 51 have the same configurations as in the prior art and, hence, they are identified by like numerals and their explanation is not repeated.

The main program 550 is an overall measurement managing program and has two selectable modes, namely a first mode for setting the sound velocity in steel and a second mode for measuring the percent spheroidicity of graphite in castings. In response to either mode, the main program activates other programs and controls the order in which they are executed.

The sound-velocity-in-steel program 511 is a sub-program for setting the sound velocity in steel, which serves as a reference value. The value of sound velocity that is measured with the sound velocity measuring program 51 and which is stored in area V is transferred by the program 511 into area Vm in RAM 6, where it is set as the sound velocity in steel.

The sound velocity normalizing program 512 is a sub-program for computing the sound velocity ratio. The value of sound velocity that is measured with the sound velocity measuring program 51 and which is stored in area V is divided by the sound velocity in steel which is stored as the reference value in area Vm, and the thusly computed sound velocity ratio is placed by the program 512 in area (V/Vm) in RAM 6.

The percent spheroidicity computing program 523 is a sub-program for computing the percent spheroidicity of graphite; it performs a conversion process in accordance with the (V/Vm)–S conversion formula 530 and computes the percent spheroidicity of graphite from the value of the sound velocity ratio in area (V/Vm). The thusly computed percent spheroidicity of graphite is stored in area S in RAM 6.

The (V/Vm)–S conversion formula 530 is an experimentally predetermined conversion formula and represents the relationship that the percent spheroidicity of graphite (s) has with respect to the sound velocity ratio between the steel and cast product ((V/Vm)).

Stated more specifically, a number of cast products are first provided that resemble each other in shape as closely as possible, and at least one steel product is also provided. Then, the sound velocity in these cast and steel products is measured with an apparatus for ultrasonic measurement, and the sound velocity ratio computed between the cast and steel products. Further, the percent spheroidicity of graphite in each cast product is measured by a direct method in accordance with or as adapted from JIS specifications. It should be noted that, in order to ensure agreement in the tendency of variations, the series of destructive measurements are desirably performed with the same apparatus for ultrasonic measurement by the same inspector if possible.

Since this direct measurement is time-consuming, it is recommended that another series of measurements be performed in parallel on another group of cast products and on at least one steel product by another set of apparatus for ultrasonic measurement and by another inspector so as to yield a large number of measurement results.

The thusly obtained large number of measurement results are plotted in relevant positions on a coordinate system, the horizontal axis of which may typically represent the sound velocity ratio ((V/Vm)) while the vertical axis represents the percent spheroidicity of graphite (S) as measured by direct means.

In this case, the sound velocity ratio as the normalized sound velocity is taken on the horizontal axis and, since it is free from any effects due to the apparatus and inspector, the results of the above-mentioned series of measurement and those of another series of measurement may be presented on one graphic chart without causing any inconvenience. Hence, the distribution diagram having its statistical reliability improved as a result of plotting the results of a large number of measurements, can be expressed by a regression line or approximated by a kinked line to yield the (V/Vm)–S conversion formula 530. For the same reason, the conversion formula 530 is in no way limited to a particular apparatus and, once it is computed, is applicable as such to any other types of apparatus for ultrasonic measurement.

With this configuration, the process of measuring the percent spheroidicity of graphite in castings starts with measuring the sound velocity in a steel product in mode 1 (the mode for setting the sound velocity in steel), followed by processing cast products successively in mode 2 (the mode for measuring the percent spheroidicity of graphite in castings).

Stated in detail, a steel product that is as similar as possible in shape to the cast products is provided as specimen 1a. Then, the main program 550 is instructed to perform processing in mode 1. In this mode 1, the main program 550 activates the sound velocity measuring program 51 and the sound velocity in the steel product is stored in area V. Then, the sound-velocity-in-steel setting program 511 as activated by the main program 550 sets the resulting sound velocity in the steel product in area Vm. In the case where the sound velocity in steel was already measured under the same conditions on the previous day or the like, the sound velocity measurement may be omitted and alternatively a predetermined value of sound velocity in steel that has been entered via keyboard 7 may be set in area Vm.

Next, one of the cast products is used as specimen 1a. Then, the main program 550 is instructed to perform processing in mode 2. In this mode 2, the main program 550 activates the sound velocity measuring program 51, and the sound velocity in the cast product being analyzed is stored in area V. Thereafter, the main program 550 activates the sound velocity normalizing program 512, and the sound velocity ratio as computed from the sound velocity (V) in the cast product being analyzed and the sound velocity (Vm) in steel is set in area (V/Vm).

Subsequently, the percent spheroidicity computing program 523 is activated, and this program 523 performs a conversion process in accordance with the (V/Vm)–S conversion formula 530 and computes the percent spheroidicity of graphite (S) from the value of sound velocity ratio in area (V/Vm). The thusly computed percent spheroidicity of graphite is stored in area S in RAM 6.

The reliable percent spheroidicity of graphite as computed from the normalized sound velocity ratio on the basis of the normalized empirical formula 530 is displayed on CRT 8 by the main program 550 as the result of measurement.

Thus, an approximate value of the percent spheroidicity of graphite in one cast product can be measured with high reliability in a nondestructive and easy manner.

Since the sound velocity in the steel product need be measured only once, each of the remaining cast products may be used successively as specimen 1a for subsequent measurements of the percent spheroidicity of graphite.

It should be mentioned that the percent spheroidicity of graphite is given to illustrate one characteristic value in connection with the physical characteristics of castings, and the operational effect of normalization by the sound velocity in steel will hold equally with other physical characteristic values of castings.

Figure 2:
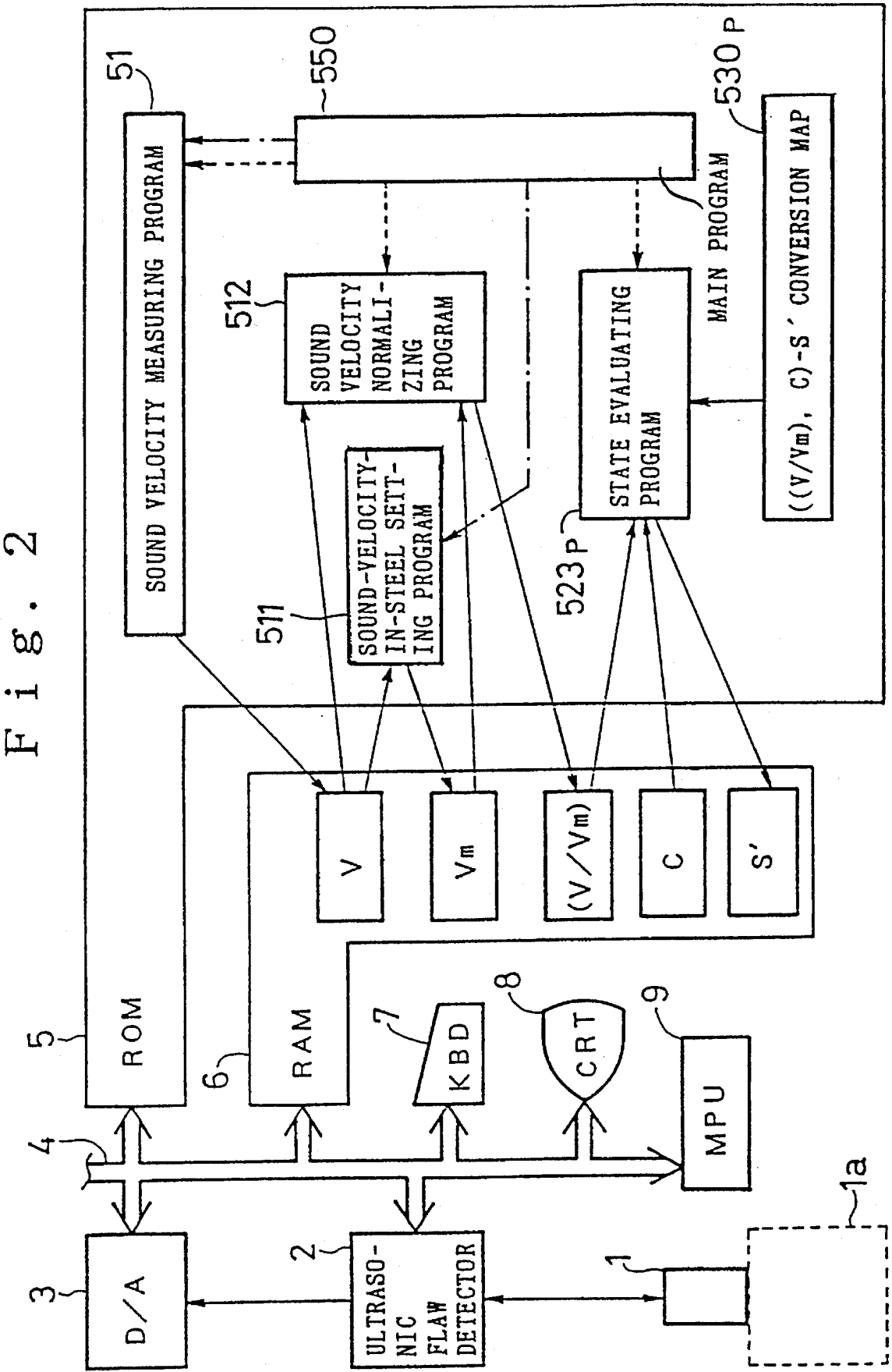
FIG. 2 is a block diagram showing a second example of the apparatus for ultrasonic measurement which features the constitution of the present invention, and which analyzes automatically the state of casting structure.

A second example of the present invention is described below in detail with reference to the drawings. FIG. 2 is a block diagram showing an apparatus for implementing the method of the present invention for analyzing the state of casting structure, namely, an apparatus for ultrasonic measurement that measures the sound velocity in a cast specimen by ultrasonic energy and which analyzes automatically the state of casting structure in the specimen.

To explain the constituent elements that differ from those shown in FIG. 1, the percent spheroidicity computing program 523 is replaced by a state evaluating program 523p, and the (V/Vm)–S conversion map 530 is replaced by a ((V/Vm),C)–S' conversion map 530p; the program is stored in ROM 5 and processed for execution by MPU 9 to perform the function it is assigned.

The main program 550 has both the first mode for setting the sound velocity in steel and the second mode for analyzing the state of casting structure. In response to either mode, the main program 550 activates other programs and controls the order in which they are executed.

The state evaluating program 523p is a sub-program for evaluating the state of casting structure; it performs a conversion process in accordance with the ((V/Vm), C)–S' conversion map 530p and evaluates the state of casting structure on the basis of both the value of sound velocity ratio in area (V/Vm) and the value of percent carbon content in area C. The thusly evaluated state of casting structure is stored in area S' in RAM 6.

The ((V/Vm),C)–S' conversion map 530p is an experimentally predetermined conversion map and represents the relationship the state of casting structure (S') has with respect to the sound velocity ratio ((V/Vm)) between the steel and cast product, and to the present carbon content of the cast product under analysis.

Stated more specifically, a number of cast products are first provided that resemble each other in shape as closely as possible but which differ in percent carbon content, and at least one steel product is also provided. Then, the sound velocity in these cast and steel products is measured with an apparatus for ultrasonic measurement, and the sound velocity ratio between the cast and steel products is computed. Further, a direct method is used in accordance with or as adapted from JIS specifications to measure the state of casting structure, for instance, to check whether the morphology of graphite grains in each cast product is like flakes, vermicular, or spheroids (FC, FCV, FCD). It should be noted that, in order to ensure agreement in the tendency of variations, the series of destructive measurements are desirably performed with the same apparatus for ultrasonic measurement by the same inspector if possible.

Since this direct measurement is time-consuming, it is recommended that another series of measurements be performed in parallel on another group of cast products and on at least one steel product by another set of apparatus for ultrasonic measurement and inspector so as to yield a large number of results of measurement.

The thusly obtained large number of measurement results are plotted in a coordinate system, with the horizontal axis typically plotting the sound velocity ratio (V/Vm) and the vertical axis plotting the percent carbon content (C), and the state of casting structure (FC, FCV, FCD) as evaluated by a direct means of measurement is set in a coordinate position that corresponds to the sound velocity ratio and the percent carbon content at the time of measurement under consideration.

If, in this case, the sound velocity ratio is plotted on the horizontal line, any effects due to the apparatus and inspector are eliminated, and an even higher probability is assured than in the case where merely the sound velocity is adopted.

It is recommended that the state of casting structure to be set is preferably freed of variable components by performing statistical processing such as decision making by majority, averaging, local averaging, or regression analysis on the results of the largest possible number of measurements. The state of casting structure may be exemplified by the hardness coefficient (m) and the above-mentioned morphological classification of graphite grains (FC, FCV, FCD); if desired, the percent spheroidicity of graphite in accordance with specifications of the JIS (Japanese Industrial Standards) may be adopted.

Figure 3:
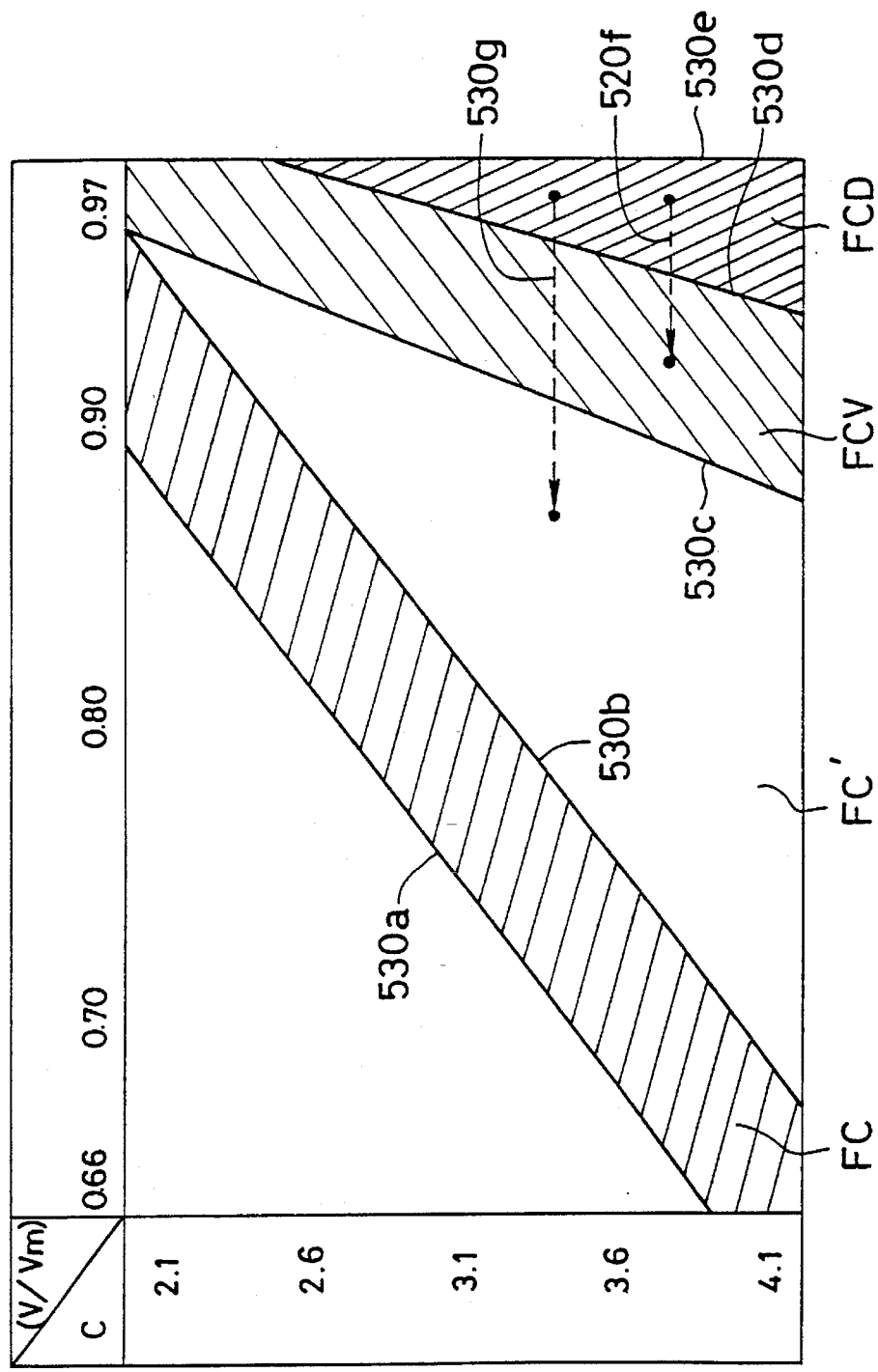
FIG. 3, relating to the second example, shows an example of the associated conversion map.

The adoption of the map which is based on the sound velocity and percent carbon content enables various regions to be clearly separated although they have been found to overlap partly according to the conventional classification, which is based solely on the sound velocity. Further, in addition, it is possible to classify even the state of casting structure in a region intermediate between two regions FC and FCV (see region FC' in FIG. 3).

With this configuration, the process of measuring the state of casting structure starts with measuring the sound velocity in a steel product in a mode 1 (the mode for setting the sound velocity in steel), followed by processing cast products successively in mode 2 (the mode for measuring the percent spheroidicity of graphite in castings).

To state in detail, without regard to partial overlap with the already-described first example, a steel product that is as similar as possible in shape to the cast products is provided as specimen 1a. Then, the main program 550 is instructed to perform processing in mode 1. In this mode 1, the main program 550 activates the sound velocity measuring program 51, and the sound velocity in the steel product is stored in area V. Then, the sound-velocity-in-steel setting program 511 as activated by the main program 550 sets the resulting sound velocity in steel product in area Vm. In the case where the sound velocity in steel was already measured under the same conditions on the previous day or the like, the sound velocity measurement may be omitted, and alternatively a predetermined value of sound velocity in steel that has been entered via keyboard 7 may be set in area Vm.

Next, one of the cast products is used as specimen 1a. Then, the main program 550 is instructed to perform processing in mode 2. In the first step of this mode 2, the percent carbon content of cast specimen 1a (which is known as one of the data for the casting operation) is entered via keyboard 7 and set in area (C). If this data entry is omitted, processing is performed on the assumption that the percent carbon content is the same as that of the previous specimen. In the subsequent second step, the main program 550 activates the sound velocity measuring program 51, and the sound velocity in the cast product being analyzed is stored in area V. Thereafter, in the third step, the main program 550 activates the sound velocity normalizing program 512, and the sound velocity ratio as computed from the sound velocity (V) in the cast product being analyzed and the sound velocity (Vm) in steel is set in area (V/Vm).

Subsequently, in the fourth step, the state evaluating program 523p is activated, and this program 523p performs a conversion process in accordance with the ((V/Vm),C)–S' conversion map 530*p* and evaluates the state of casting structure in terms of the value of the position in the map that corresponds to the value of sound velocity ratio in area (V/Vm) and the value of percent carbon content in area (C). The thusly evaluated state of casting structure is stored in area S in RAM 6.

The reliable state of casting structure, as evaluated by close classification with respect to the sound velocity ratio and percent carbon content on the basis of the conversion map 530*p*, is displayed on CRT 8 by the main program 550 as the result of measurement. For instance, if heats that have been adjusted in components and the like with a view to producing spheroidal graphite cast iron having high toughness turn into CV cast iron of lower toughness or flaky cast iron as a result of delay in processing time or the like (see arrows 520*f* and 530*g* in FIG. 3), this fact and the like can be detected in a positive and nondestructive manner.

Thus, the state of casting structure can be analyzed on a single cast product with high reliability in a nondestructive and easy manner.

Since the sound velocity in the steel product need be measured only once, each of the remaining cast products may successively be used as specimen 1*a* for subsequent analyses of the state of casting structure on those products.

Figure 4:
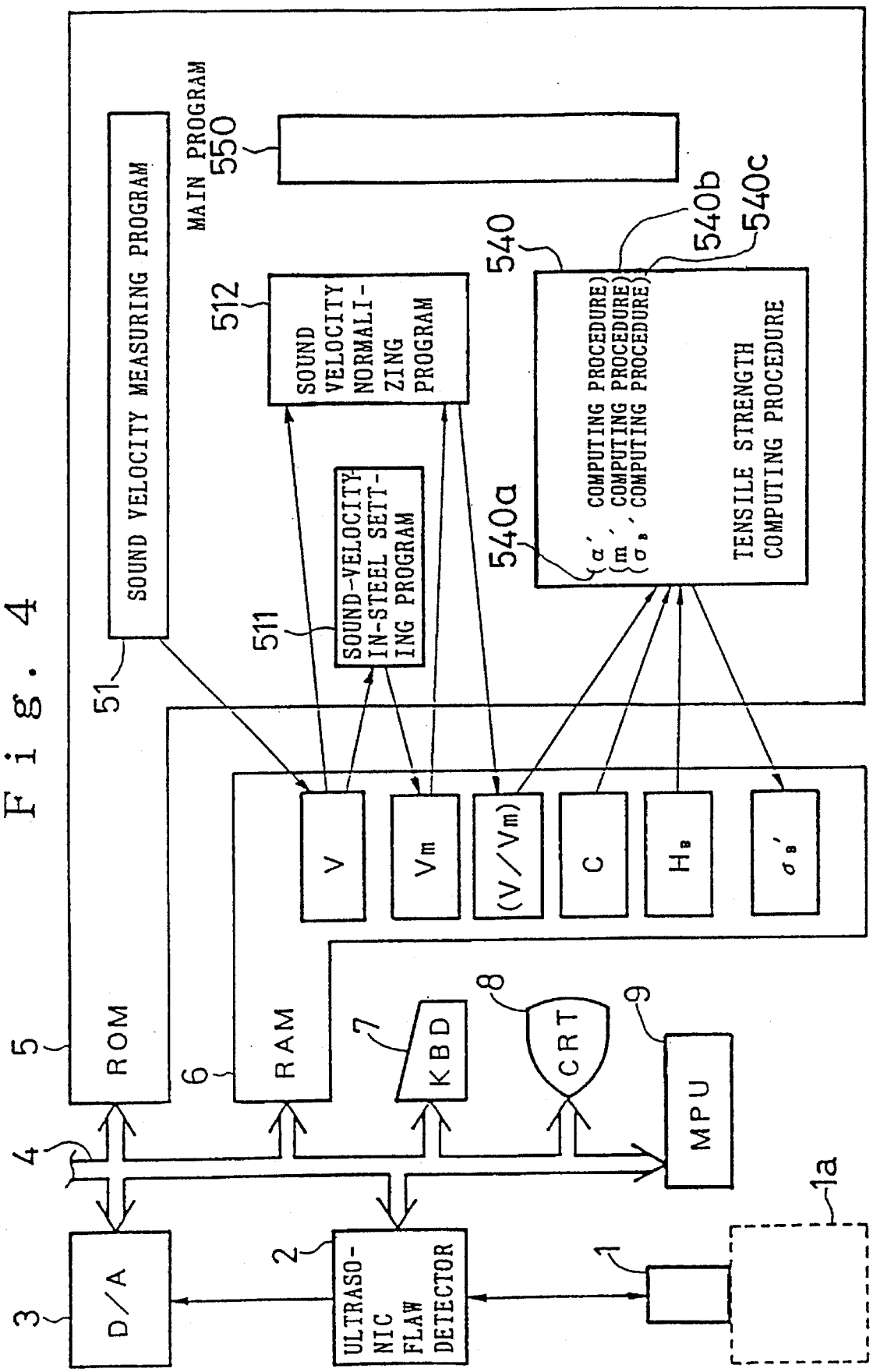
FIG. 4 is a block diagram showing a third example of the apparatus for ultrasonic measurement which features the constitution of the present invention, and which measures or computes automatically the tensile strength of a cast product.

A third example of the present invention is described below with reference to the drawings. FIG. 4 is a block diagram of an apparatus for ultrasonic measurement that measures the sound velocity in a cast specimen by ultrasonic wave energy, and which computes automatically the tensile strength of that specimen.

The configuration of this apparatus is basically similar to that of the already-described second example, except that the state evaluating program 523 in the second example is replaced by a new program 540 and associated elements for computing the tensile strength.

To explain the constituent elements that differ from those shown in FIG. 2, the tensile strength computing program 540 is a sub-program for computing the tensile strength of castings; it performs a specified conversion process to compute the tensile strength of a cast product on the basis of three values: the value of sound velocity ratio in area (V/Vm), the value of percent carbon content in area C, and the value of Brinell hardness in area HB. The thusly computed tensile strength of the cast product is stored in area σB' in RAM 6.

The specified conversion process is an experimentally predetermined computing procedure for computing the tensile strength (σB') of a cast product on the basis of the relationship that its tensile strength (σB) has with respect to the sound velocity ratio (V/Vm) between the steel and cast product, the percent carbon content (C) of the cast product under analysis, and its Brinell hardness (HB).

This computing procedure comprises mainly an α' computing procedure 540*a*, an m' computing procedure 540*b*, and a σB' computing procedure 540*c*. In the example under discussion, these procedures are incorporated as part of the tensile strength computing program 540 and they are executed in the order written.

The α computing procedure 540*a* is so specified as to express the relationship that the state of casting structure (FCD, FCV, FC) has with respect to the sound velocity ratio ((V/Vm)) and the percent carbon content (C).

The actual process of specifying the computing procedure of interest starts with providing a number of cast products that resemble each other in shape as closely as possible but which differ in percent carbon content, and also providing at least one steel product. Then, the sound velocity in these cast and steel products is measured with an apparatus for ultrasonic measurement, and the sound velocity ratio between the cast and steel products is computed. Further, a direct method is used in accordance with or as adapted from JIS specifications to measure the state of casting structure, for instance, to check whether the morphology of graphite grains in each cast product is like flakes, vermicular, or spheroids (FC, FCV, FCD), or whether they are in a state intermediate between these types. It should be noted that in order to ensure agreement in the tendency of variations, the series of destructive measurements are desirably performed with the same apparatus for ultrasonic measurement by the same inspector if possible.

Since this direct measurement is time-consuming, it is recommended that another series of measurements be performed in parallel on another group of cast products and at least one steel product by another set of apparatus for ultrasonic measurement and inspector so as to yield a large number of measurement results.

It is also recommended that the index value for the state of casting structure to be set be preferably one that is free of variable components, by performing statistical processing such as decision making by majority, averaging, local averaging, or regression analysis on the results of the largest possible number of measurements.

The α' computing procedure 540*a*, as a specific example of the way to compute the index value, proceeds as follows. First, on the basis of the sound velocity ratio ((V/Vm)) and the percent carbon content (C), the density p is computed by the equation:

$$\rho = 8.435 - 0.374 \times (C)$$

Then, the graphite area factor is computed by the equation:

$$fg = 1.095 - 0.1395 \times \rho$$

Finally, α' is computed by the equation:

$$\alpha' = ((V/Vm)^2 \times (7.86/\rho) - 1)/fg$$

It should be noted that the value 7.86 in the above equation is equivalent to the specific gravity of the steel product or the casting matrix (base).

Figure 5:
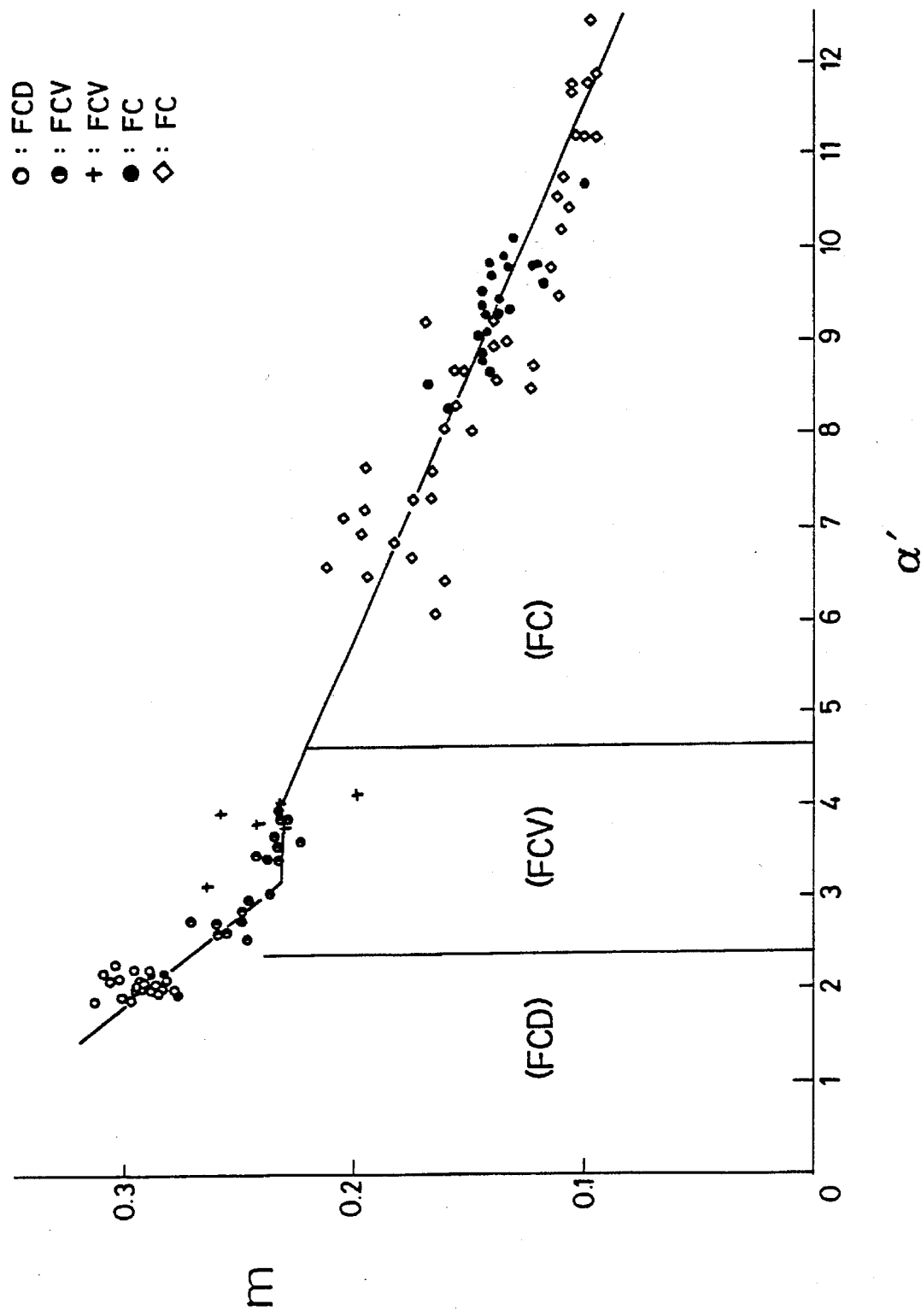
FIG. 5, relating to the third example, shows in graphic form the correspondence between the computed index value $\alpha'$ of the cast product (horizontal axis) and the measured hardness coefficient m (vertical axis)

The thusly computed α' is the index value for the state of casting structure that is based on the morphological classification of graphite grains in the cast product (FC, FCV, FCD), and yet it is capable of clearly identifying a state intermediate between those types (see the horizontal axis α' of FIG. 5 and the distribution of data on the measurement).

The m' computing procedure 540*b* is a procedure for computing the hardness coefficient m' from the index value α'. The hardness coefficient m' is an estimated value of hardness coefficient m, namely (tensile strength σB/hardness HB), and is determined from the index value α' in accordance with the relationship between index value α' and hardness coefficient m that has been verified preliminarily on an experimental basis. This relationship is shown in FIG. 5, with the index value α' plotted on the horizontal axis and the hardness coefficient m on the vertical axis. Since there is a strong correlation between α' and m in FIG. 5, the relationship under consideration can be approximated by a kinked line or the like.

To give a specific example, the m' computing procedure 540*b* computes the hardness coefficient m' by the following criteria:

In the case of α'<3.15, computation is performed by the equation:

$$m'=0.3920-0.0512\times\alpha';$$

in the case of 3.15≦α'≦4.00, computation is performed by the equation:

$$m'=0.2306;\text{ and}$$

in the case of 4.00<α', computation is performed by the equation:

$$m'=0.3000-0.0173\times\alpha'.$$

The hardness coefficient m' that is computed by any of these equations provides a very good estimation of the actual hardness coefficient m.

The σB' computing procedure 540c is such that the tensile strength σB', as an estimated value of tensile strength σB, is computed from the hardness HB and hardness coefficient m' on the basis of the formula for defining hardness coefficient m, namely, (m=σB/HB). Stated specifically, the procedure 540c computes the tensile strength σB' by the equation σB'=m'×HB.

The hardness coefficient m is introduced to replace the cumbersome measurement of the true percent spheroidicity of graphite by the easier method of computation or estimation on the basis of a tensile fracture test. In the example under discussion, the role of this coefficient is expanded on the basis of experimental results and, from the relationship it has, the tensile strength σB' is computed in the manner described above.

With this configuration, the process of measuring the tensile strength of a cast product starts with measuring the sound velocity in a steel product in mode 1 (the mode for setting the sound velocity in steel), followed by processing cast products successively in mode 2 (the mode for measuring the percent spheroidicity of graphite in castings).

Mode 1 is entirely the same as in the previous examples and, hence, need not be described in detail. It should only be mentioned that in mode 1, the sound velocity in the steel product is set in area Vm.

In the next place, one of the cast products is used as specimen 1a. Then, the main program 550 is instructed to perform processing in mode 2.

In the first step of this mode 2, the percent carbon content of the cast specimen 1a (which is known as one of the data for the casting operation) is entered via keyboard 7 and set in area (C). If this data entry is omitted, processing is performed on the assumption that the percent carbon content is the same as that of the previous specimen.

In the subsequent second step, the main program 550 activates the sound velocity measuring program 51, and the sound velocity in the cast product being analyzed is stored in area V. If the specimen 1a is in the as-cast state, the value in area V may be left as it is. However, in a different case like the one where the specimen 1a is an annealed cast product, 130 (m/s) is added as a correction value to the value of sound velocity in area V; if the specimen 1a is a normalized cast product, 400 (m/s) typically may be added. This correction helps further improve the probability of the computed value.

Thereafter, in the third step, the main program 550 activates the sound velocity normalizing program 512, and the sound velocity ratio as computed from the sound velocity (v) in the cast product being analyzed and the sound velocity (Vm) in steel is set in area (V/Vm).

Subsequently, in the fourth step, the Brinell hardness of the specimen 1a as measured with a separate hardness tester is entered via keyboard 7 and set in area HB. Then, the tensile strength computing program 540 is activated by the main program 550.

The tensile strength computing program 540 executes the α' computing procedure 540a, m' computing procedure 540b, and σB' computing procedure 540c in that order, and computes the tensile strength on the basis of the sound velocity ratio (V/Vm), percent carbon content (C), and Brinell hardness (HB) that have been measured on the specimen 1a. The thusly computed tensile strength is stored in area σB' in RAM 6.

The fourth step is described below in detail. First, the index value α' is computed by the α' computing procedure 540a on the basis of the sound velocity ratio (V/Vm) and percent carbon content (C). It should be noted here that, if C is smaller than 9.0495−7.1189×(V/Vm) when computing α', the percent carbon content (C) must be replaced beforehand by the value expressed by the equation:

$$8.7995-7.1189\times(V/Vm)$$

This condition is applicable to the case where the cast product under analysis corresponds to gray cast iron (FC), particularly to a typical example of it; this correction of C helps further improve the probability of the computed value.

In the next place, the m' computing procedure 540b computes the hardness coefficient m' from the above α'. Then, except in the case of the already evaluated gray cast iron which is mentioned above, the state of casting structure is classified on the basis of the value index α' or the value of hardness coefficient m'. For example, if 0.27≦m', the cast product under analysis is evaluated as being made of spheroidal graphite cast iron (FCD); in the case of 0.22≦m'<0.27, it is found to be made of worm-like graphite cast iron (FCV); and if m'<0.22, it is found to be made of flaky graphite cast iron (FCD).

Finally, the tensile strength (σB') is computed from the above-mentioned hardness coefficient m' and Brinell hardness (HB) by the σB' computing procedure 540c.

Figure 6:
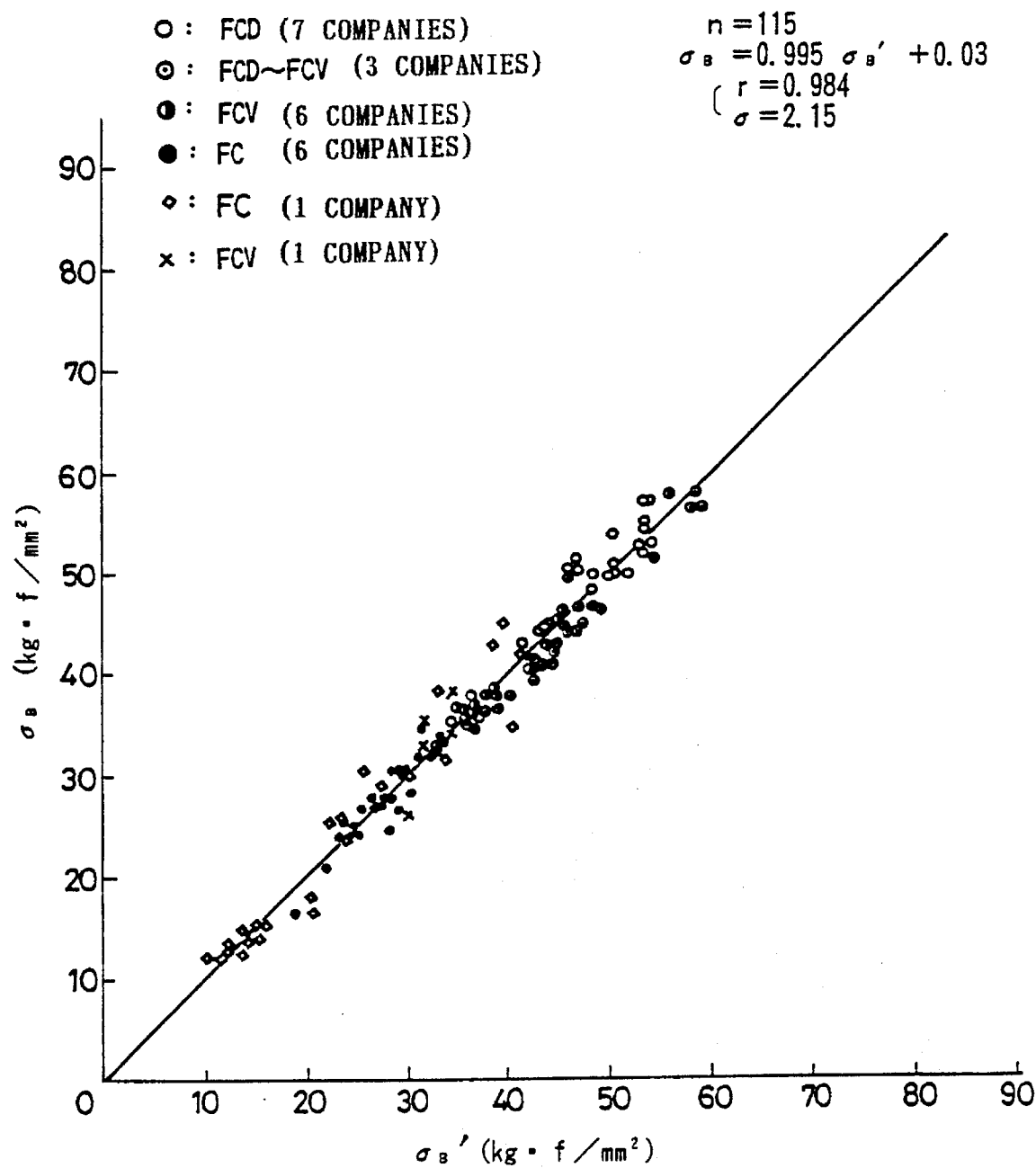
FIG. 6, relating to the third example, shows in graphic form the correspondence between the computed tensile strength $\sigma B'$ (horizontal axis) and the measured tensile strength $\sigma B$ (vertical axis)

The correspondence between the thusly computed tensile strength (σB') and the tensile strength (σB) that was measured directly by a tensile test is shown in FIG. 6. As is clear from the FIG. 6 graph, the tensile strength of castings that was computed by means of the apparatus of the present invention for ultrasonic measurement has an extremely high probability. For instance, the estimated precision based on variance is 2.15 (kgf/mm$^2$). This is comparable to the estimated precision 1.93 (kgf/mm$^2$) for normalized or annealed steel products, which is used extensively in designs using steel, whereas it is far better than the estimated precision 3.41 (kgf/mm$^2$) for quenched and tempered steel products, which is also used extensively.

The tensile strength (σB') as well as the state of casting structure (FCD, FCV, FC) are displayed on CRT 8 by the main program 550 as the result of measurement and analysis.

This ensures the following and other facts to be detected in a positive and nondestructive manner: For example, heats that have been adjusted in components and the like with a view to producing spheroidal graphite cast iron having high tensile strength or toughness turn out to be short of the intended tensile strength or, in certain cases, turn into CV cast iron or flaky cast iron of lower strength as a result of delay in processing time or the like.

Thus, the tensile strength of castings can be measured or computed on a single cast product with high reliability in a nondestructive and easy manner.

In addition, the sound velocity in the steel product need be measured only once and, hence, each of the remaining cast products may be used successively as specimen 1a for subsequent analyses of the state of casting structure and measurements of tensile strength on those products.

Figure 7:
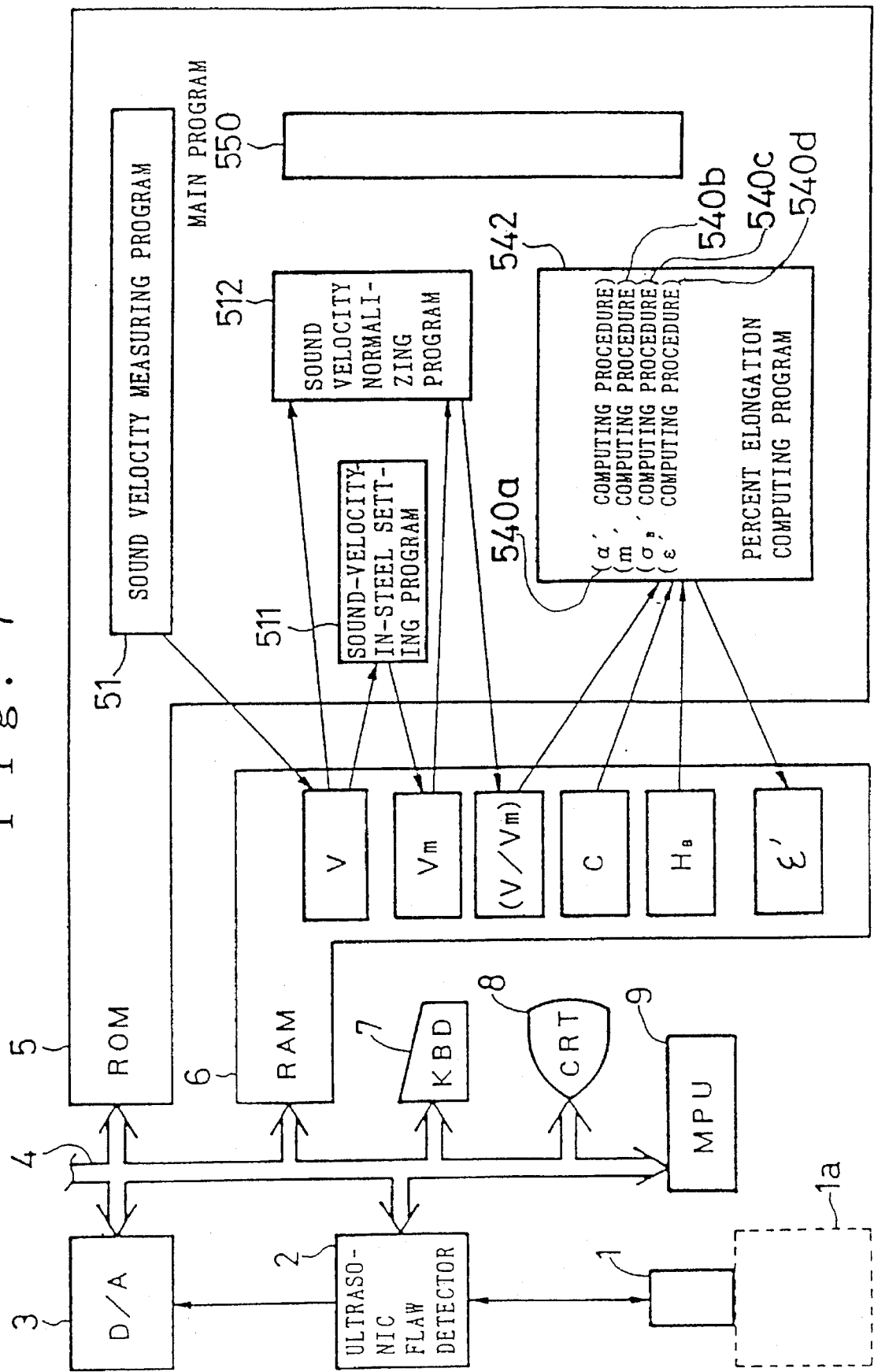
FIG. 7 is a block diagram showing a fourth example of the apparatus for ultrasonic measurement which features the constitution of the present invention, and which measures or computes automatically the percent elongation of a cast product.

A fourth example of the present invention is described below with reference to the drawings. FIG. 7 is a block diagram of an apparatus for implementing the method of the present invention for measuring the percent elongation of castings, namely, an apparatus for ultrasonic measurement that measures the sound velocity in a cast specimen by ultrasonic wave energy, and which computes automatically the percent elongation of that specimen.

The configuration of this apparatus is basically similar to that of the already-described third example except that the tensile strength computing program 540 in the third example is replaced by a new program 542 and associated elements for computing the percent elongation.

The following explanation centers on the differences from the example shown in FIG. 4. The percent elongation computing program 542 is substantially similar to the already-described tensile strength computing program 540 as regards the basic configuration and the technical rationale; it is a sub-program that performs a specified measurement and a specified conversion process to compute the percent elongation of a cast product. Further, the specific configurations of the two programs are similar in that each has the $\alpha'$ computing procedure 540a, m' computing procedure 540b, and $\sigma B'$ computing procedure 540c, and that these procedures are executed in the order written.

However, the program 542 differs from the tensile strength computing program 540 in that it has an additional $\epsilon'$ computing procedure 540d for computing the percent elongation in the last step. Stated more specifically, the program 542 performs a specified conversion process and computes the percent elongation of a cast product on the basis of three values: the value of sound velocity ratio in area (V/Vm), the value of percent carbon content in area C, and the value of Brinell hardness in area HB. The thusly computed elongation of the cast product is stored in area $\epsilon'$ in RAM 6.

The specified conversion process under consideration is an experimentally predetermined computing procedure for computing the percent elongation ($\epsilon'$) of the cast product on the basis of the relationship that its percent elongation ($\epsilon$) has with respect to the sound velocity ratio ((V/Vm)) between the steel and the cast product, the percent carbon content (C) of the cast product under analysis, and its Brinell hardness (HB).

This computing procedure comprises mainly the $\alpha'$ computing procedure 540a, m' computing procedure 540b, $\sigma B'$ computing procedure 540c, and the $\epsilon'$ computing procedure 540d, and these procedures are executed in the order written. All procedures except the $\epsilon'$ computing procedure 540d have already been described above and discussion of them will not be repeated below.

Figure 8:
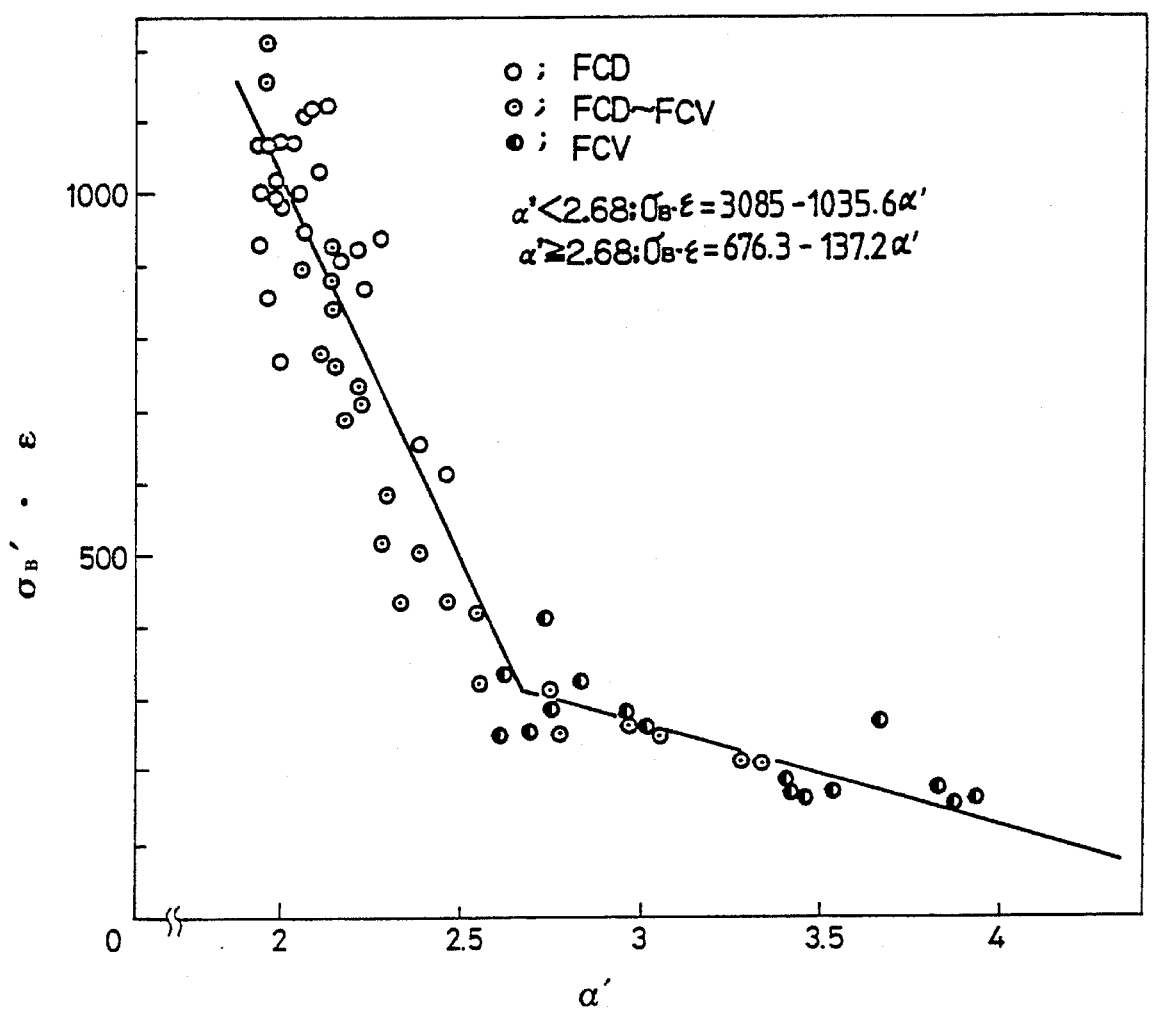
FIG. 8, relating to the fourth example, shows in graphic form the correspondence between the computed index value $\alpha'$ (horizontal axis) and the product of tensile strength $\sigma B'$ and percent elongation $\epsilon$ ($\sigma B' \times \epsilon$) (vertical axis)

The $\epsilon'$ computing procedure 540d is a procedure for computing the percent elongation $\epsilon$ from the index value $\alpha'$ and the estimated tensile strength $\sigma B'$. The percent elongation $\epsilon'$ is an estimated value of the actual percent elongation $\epsilon$, and is determined from the index value $\alpha'$ (which has been verified preliminarily on an experimental basis) and the tensile strength $\sigma B'$ (which has been computed on the basis of $\alpha'$) in accordance with the relationship between the index value $\alpha'$, the tensile strength $\sigma B'$, and the percent elongation $\epsilon$ which has been determined in a tensile test. This relationship is shown in FIG. 8, with the index value $\alpha'$ being plotted on the horizontal axis and the product of tensile strength $\sigma B'$ and percent elongation $\epsilon$ ($\sigma B' \times \epsilon$) on the vertical axis. Since there is a strong correlation between $\alpha'$ and ($\sigma B' \times \epsilon$) in FIG. 8, the relationship under consideration can be approximated by a kinked line or the like.

To give a specific example, the $\epsilon'$ computing procedure 540d computes the percent elongation $\epsilon'$ (in %) by the following criteria:

if $\alpha' < 2.68$, computation is performed by the equation:

$$\epsilon' = (3085 - 1035.6 \times \alpha') \sigma B'; \text{ and}$$

if $\alpha' \leq 2.68$, computation is performed by the equation:

$$\epsilon' = (676.3 - 137.2 \times \alpha').$$

Obviously, if these equations are rewritten by expressing the tensile strength $\sigma B'$ in terms of the above-described index value $\alpha'$, one can readily obtain formulae for computing the percent elongation $\epsilon'$ solely on the basis of the index value $\alpha'$.

The thusly computed percent elongation $\epsilon'$ provides a very good estimation of the actual percent elongation $\epsilon$.

With this configuration, the process of measuring the percent elongation of a cast product starts with measuring the sound velocity in a steel product in mode 1 (the mode for setting the sound velocity in steel), followed by processing cast products successively in mode 2 (the mode for measuring the percent elongation of castings).

Again, details of the process are substantially similar to the case of the third example, and explanation of the overlapping portions will not be repeated. The only difference from the third example is that the tensile strength of a cast product is not the sole factor to be computed in mode 2, and that the percent elongation ($\epsilon'$), which is one characteristic value of the cast product, is also computed by the percent elongation computing program 542 and outputted as the result of measurement and analysis.

Further discussion is made of this point. In mode 2, the percent elongation computing program 542, like the tensile strength computing program 540, executes the $\alpha'$ computing procedure 540a, m' computing procedure 540b, and $\sigma B'$ computing procedure 540c in that order, and computes the index value ($\alpha'$) and tensile strength ($\sigma B'$) from the sound velocity ratio (V/Vm), percent carbon content (C), and Brinell hardness (HB) which have been measured on the specimen 1a. Subsequently, the $\epsilon'$ computing procedure computes the percent elongation ($\epsilon'$) from the above-mentioned index value ($\alpha'$) and tensile strength ($\sigma B'$).

Figure 9:
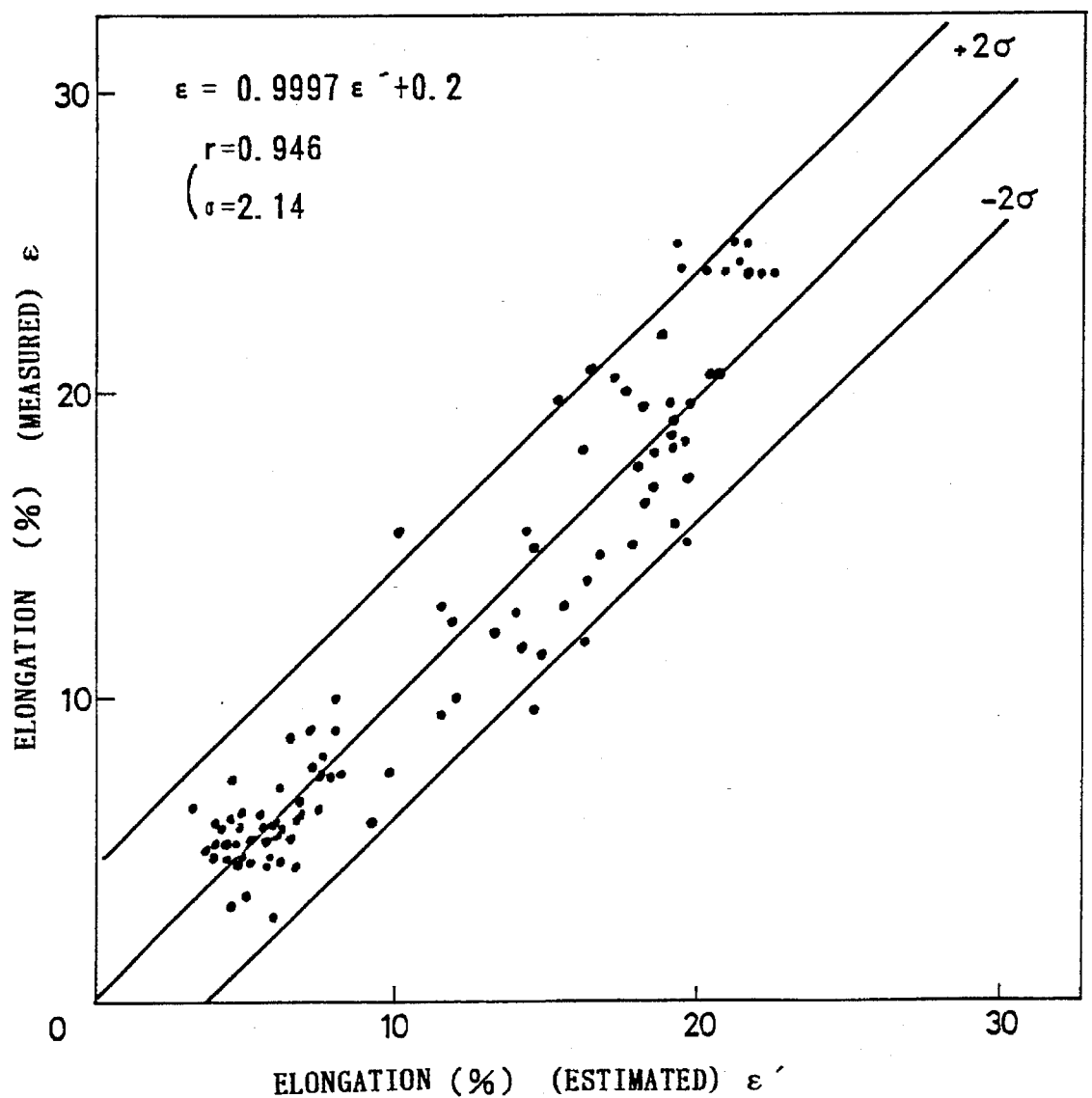
FIG. 9, relating to the fourth example, shows in graphic form the correspondence between the computed percent elongation $\epsilon'$ (horizontal axis) and the measured percent elongation $\epsilon$ (vertical axis)

The correspondence between the thusly computed percent elongation ($\epsilon'$) and the percent elongation ($\epsilon$) that was measured directly by a tensile test is shown in FIG. 9. As is clear from the FIG. 9 graph, the percent elongation of castings that was computed by means of the apparatus of the present invention for ultrasonic measurement has a fairly high probability.

This percent elongation ($\epsilon'$) as well as the state of casting structure (FCD, FCV, FC) are displayed on CRT 8 by the main program 550 as the result of measurement and analysis.

This ensures the following and other facts to be detected in a positive and nondestructive manner: For example, heats that have been adjusted in components and the like with a view to producing cast iron having high percent elongation turn out to be short of the intended percent elongation as a result of mismatch with processing or the like.

Thus, the percent elongation of castings can be measured or computed on a single cast product with high reliability in a nondestructive and easy manner.

In addition, the sound velocity in the steel product need be measured only once and, hence, each of the remaining cast products may be used successively as specimen 1a for subsequent analyses of the state of casting structure and measurements of percent elongation on those products.

Figure 10:
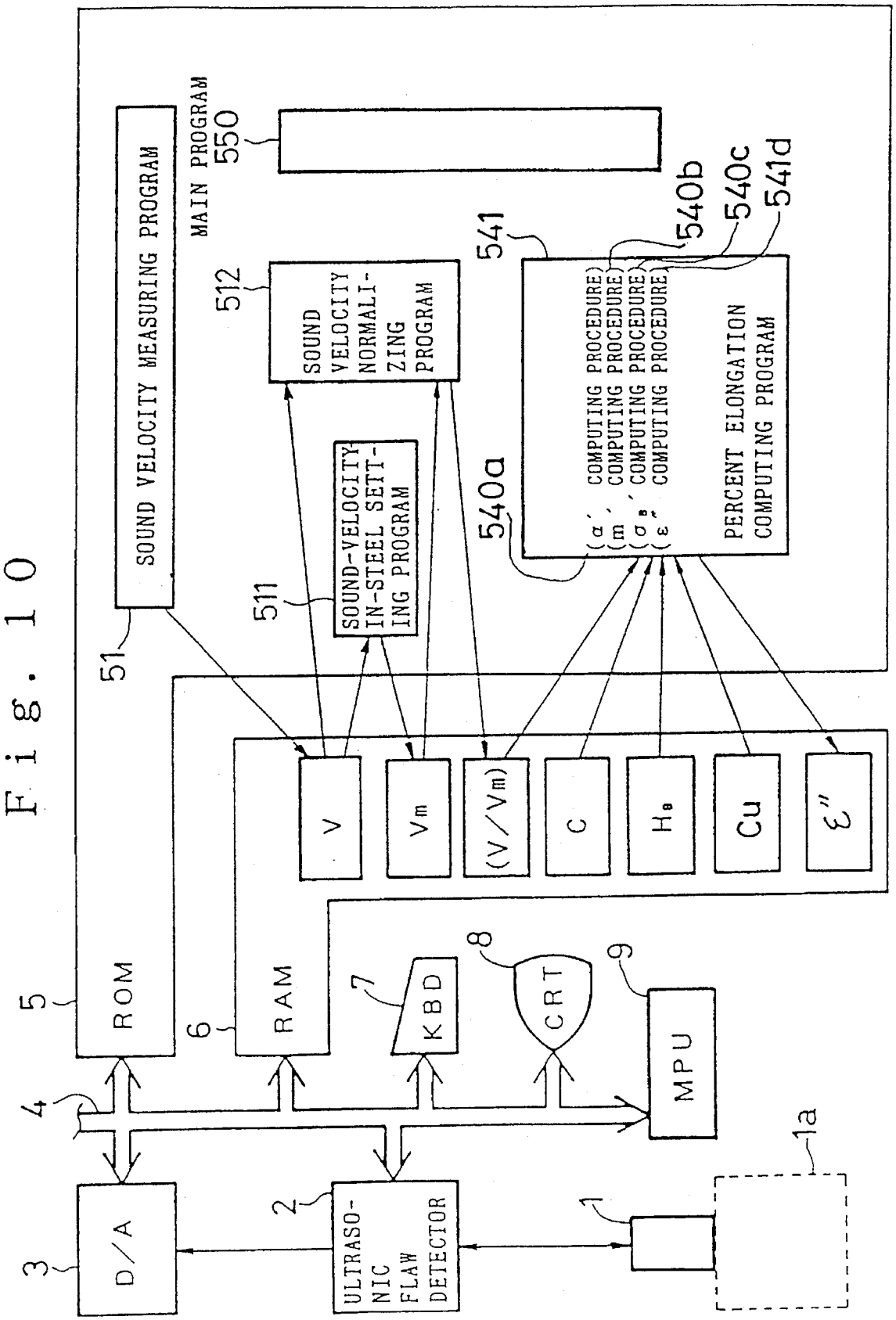
FIG. 10 is a block diagram showing a fifth example of the apparatus for ultrasonic measurement which features the constitution of the present invention, and which measures or computes automatically the percent elongation of a copper-containing cast iron.

A fifth example of the present invention is described below with reference to the drawings. FIG. 10 is a block diagram of an apparatus for ultrasonic measurement that is particularly advantageous for use on copper-containing cast iron. For the especial purpose of assuring enhanced tensile strength, copper is sometimes contained in castings at significant levels of about 1% and, in the case of such copper-containing cast iron, the empirical formula to be used differs slightly from the case just described above, and is necessary to make corrections in accordance with the present copper content.

The configuration of the apparatus under consideration is basically similar to that of the already-described fourth example, except that the $\epsilon'$ computing procedure in the percent elongation computing program used in the fourth example is replaced by a new procedure and associated elements for computing $\epsilon''$.

The following explanation centers on the differences from the example shown in FIG. 7. The percent elongation computing program 541 is substantially similar to the already-described percent elongation computing program 540 as regards the basic configuration and the technical rationale; it is a sub-program that performs a specified measurement and a specified conversion process to compute the percent elongation of a cast product. However, the program 541 differs from the percent elongation computing program 540 in that the cast product to be measured is limited to copper-containing cast iron, and in that the percent elongation of the cast product is computed not simply from the values of sound velocity ratio in area (V/Vm), percent carbon content in area C, and Brinell hardness in area HB, but from the combination of these values with the percent copper content (in %). The thusly computed percent elongation of the cast product is stored in area $\epsilon''$ in RAM 6.

The specified conversion process under consideration is an experimentally predetermined computing procedure for computing the percent elongation ($\epsilon''$) of the cast product on the basis of the relationship that its percent elongation ($\epsilon$) has with respect to the sound velocity ratio ((V/Vm)) between the steel and cast product, the percent carbon content (C) of the cast product under analysis, its Brinell hardness (HB), and its percent copper content (Cu).

This computing procedure comprises mainly the already-described $\alpha'$ computing procedure 540a, m' computing procedure 540b, and $\sigma B'$ computing procedure 540c, as well as the new procedure 541d for computing $\epsilon''$. In the example under discussion, these procedures are incorporated as part of the percent elongation computing program 541 and they are executed in the order written.

Explanation of the $\alpha'$ computing procedure 540a, m' computing procedure 540b, and $\sigma B'$ computing procedure 540c is not repeated here but, as already mentioned, these programs compute $\alpha'$, m', and $\sigma B'$, respectively, from the sound velocity ration ((V/Vm)), percent carbon content (C), and Brinell hardness (HB).

Figure 11:
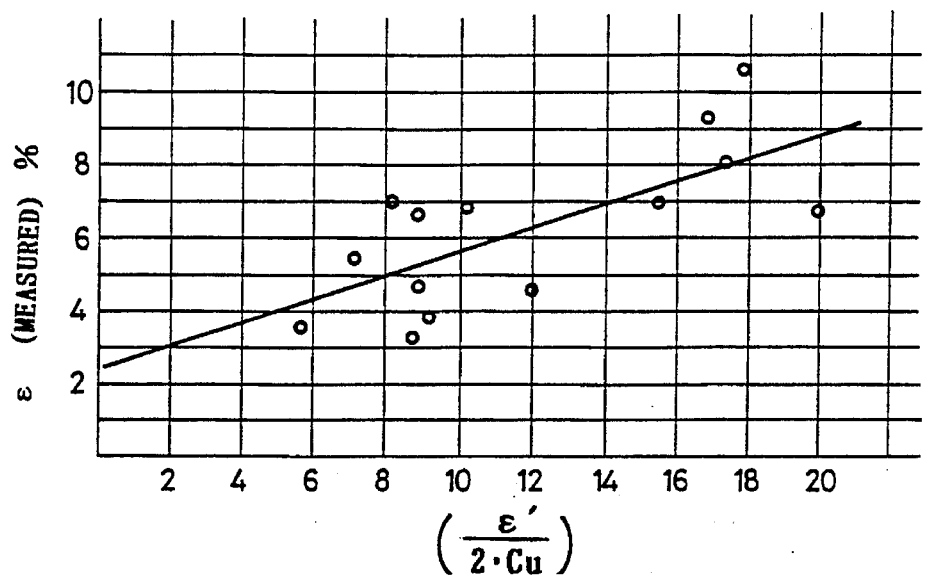
FIG. 11, relating to the fifth example, shows in graphic form the correspondence between the computed value ($\epsilon'/(2\times Cu)$) (horizontal axis) and the measured percent elongation $\epsilon$ (vertical axis)

The $\epsilon''$ computing procedure 541d is a procedure by which the percent elongation $\epsilon''$ as an estimated value of the actual percent elongation $\epsilon$ is computed from the index value $\alpha'$, estimated tensile strength $\sigma B'$, and percent copper content (Cu) To determine the percent elongation $\epsilon''$, the percent elongation $\epsilon'$ in the aforementioned example which has been computed from the index value $\alpha'$ and the estimated tensile strength $\sigma B'$ is first corrected by the percent copper content (Cu) to yield the value ($\epsilon'/(2 \times Cu)$), and this value ($\epsilon'/(2 \times Cu)$) is fitted into the relation it has with respect to the percent elongation $\epsilon$, which was determined in a tensile test. This relationship is shown in FIG. 11, with the value ($\epsilon'/(2 \times Cu)$) being plotted on the horizontal axis and the percent elongation $\epsilon$ on the vertical axis. Since there is a strong correlation between ($\epsilon'/(2 \times Cu)$) and $\epsilon$ in FIG. 11, the relationship under consideration can be approximated by a kinked line or the like.

To give a specific example, the $\epsilon''$ computing procedure 541d expresses the percent elongation $\epsilon'$ in terms of the index value $\alpha'$ and the tensile strength $\sigma B'$, and determines $\epsilon''$ from the index value $\alpha'$, tensile strength $\sigma B$, and percent carbon content (Cu in %) by the following criteria:

If $\alpha' < 2.68$, computation is performed by the equation:

$$\epsilon'' = (0.165 \times (3085 - 1035.6 \times \alpha')/(\sigma B' \times U)) + 2.3; \text{ and}$$

if $\alpha' \geq 2.68$, computation is performed by the equation:

$$\epsilon'' = (0.165 \times (676.3 - 137.2 \times \alpha')/(\sigma B' \times U)) + 2.3.$$

Thus, the percent elongation $\epsilon''$ is computed (in %).

Obviously, if the equations set forth above are rewritten by expressing the tensile strength $\sigma B'$ in terms of the above-described index value $\alpha'$, one can readily obtain formulae for computing the percent elongation $\epsilon''$ solely on the basis of the index value $\alpha'$ and the percent copper content (Cu).

Figure 12:
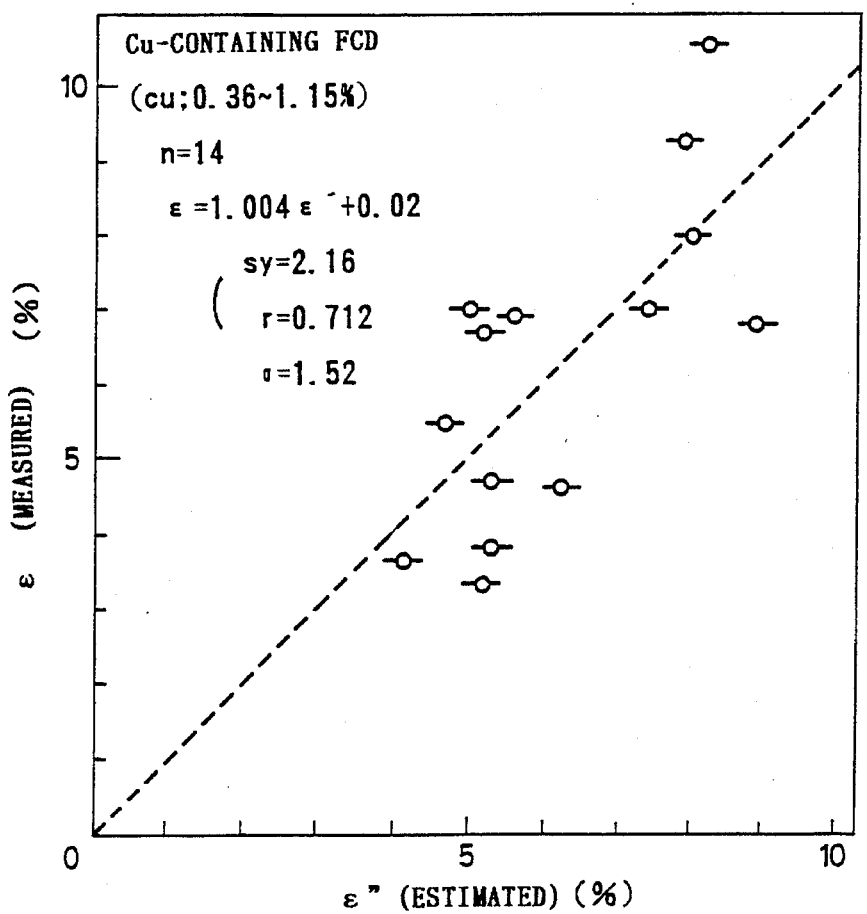
FIG. 12, relating to the fifth example, shows in graphic form the correspondence between the computed percent elongation $\epsilon''$ (horizontal axis) and the measured percent elongation $\epsilon$ (vertical axis)
Figure 13:
FIG. 13 is a diagrammatic presentation of examples of the morphology of graphite in castings.
Figure 13:
Figure 13:
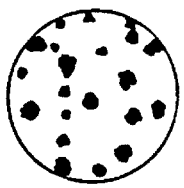
Figure 13:
Figure 13:
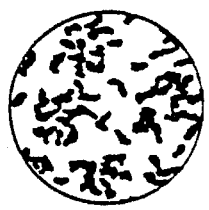
Figure 13:
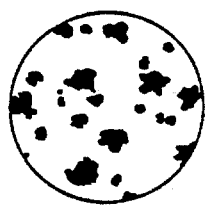
Figure 13:
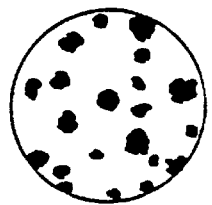
Figure 13:
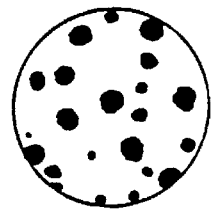
Figure 14:
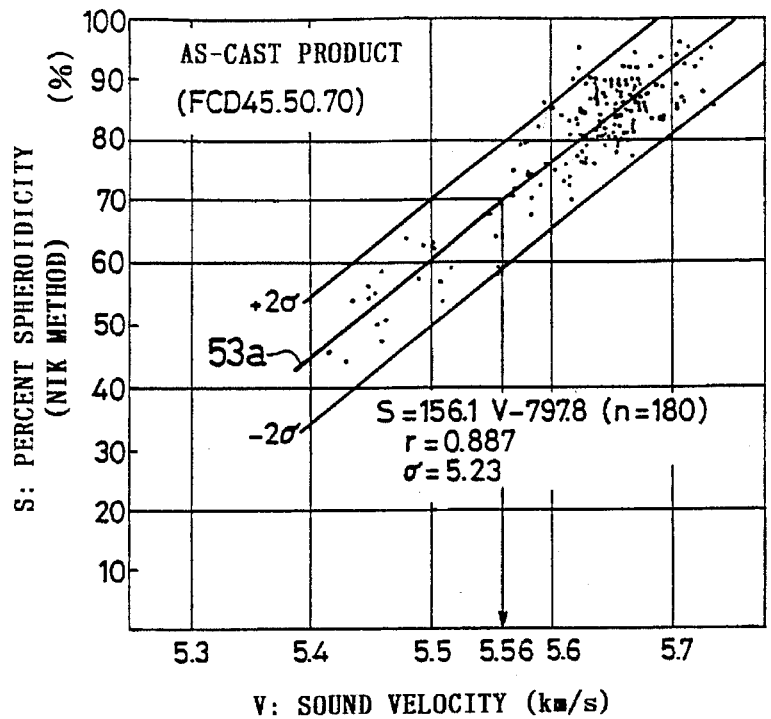
FIG. 14 is an example of the relationship between the sound velocity in castings and the percent spheroidicity of graphite.
Figure 15:
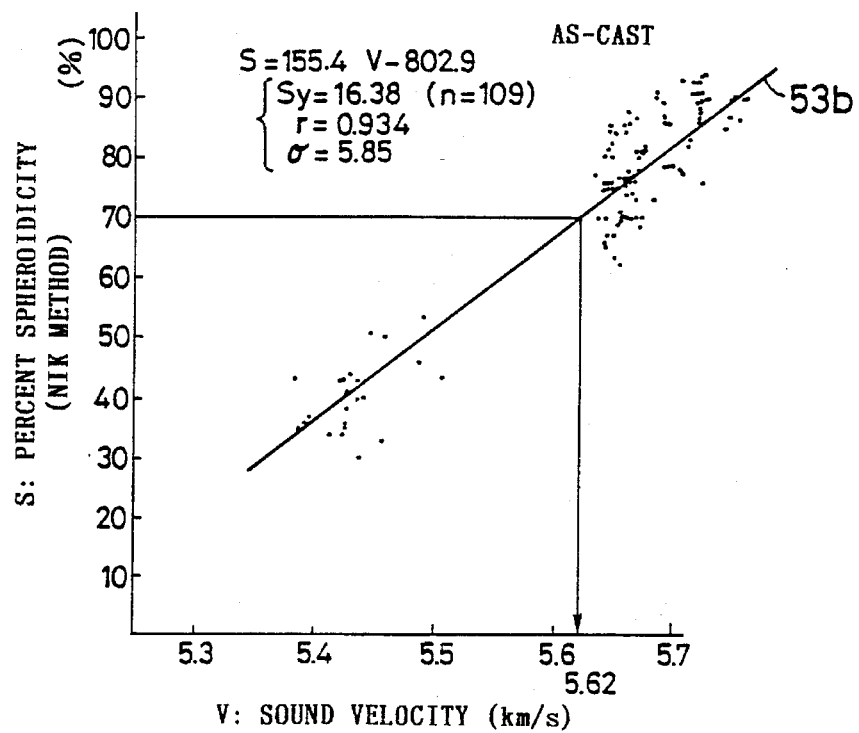
FIG. 15 is another example of the relationship between the sound velocity in castings and the percent spheroidicity of graphite.
Figure 16:
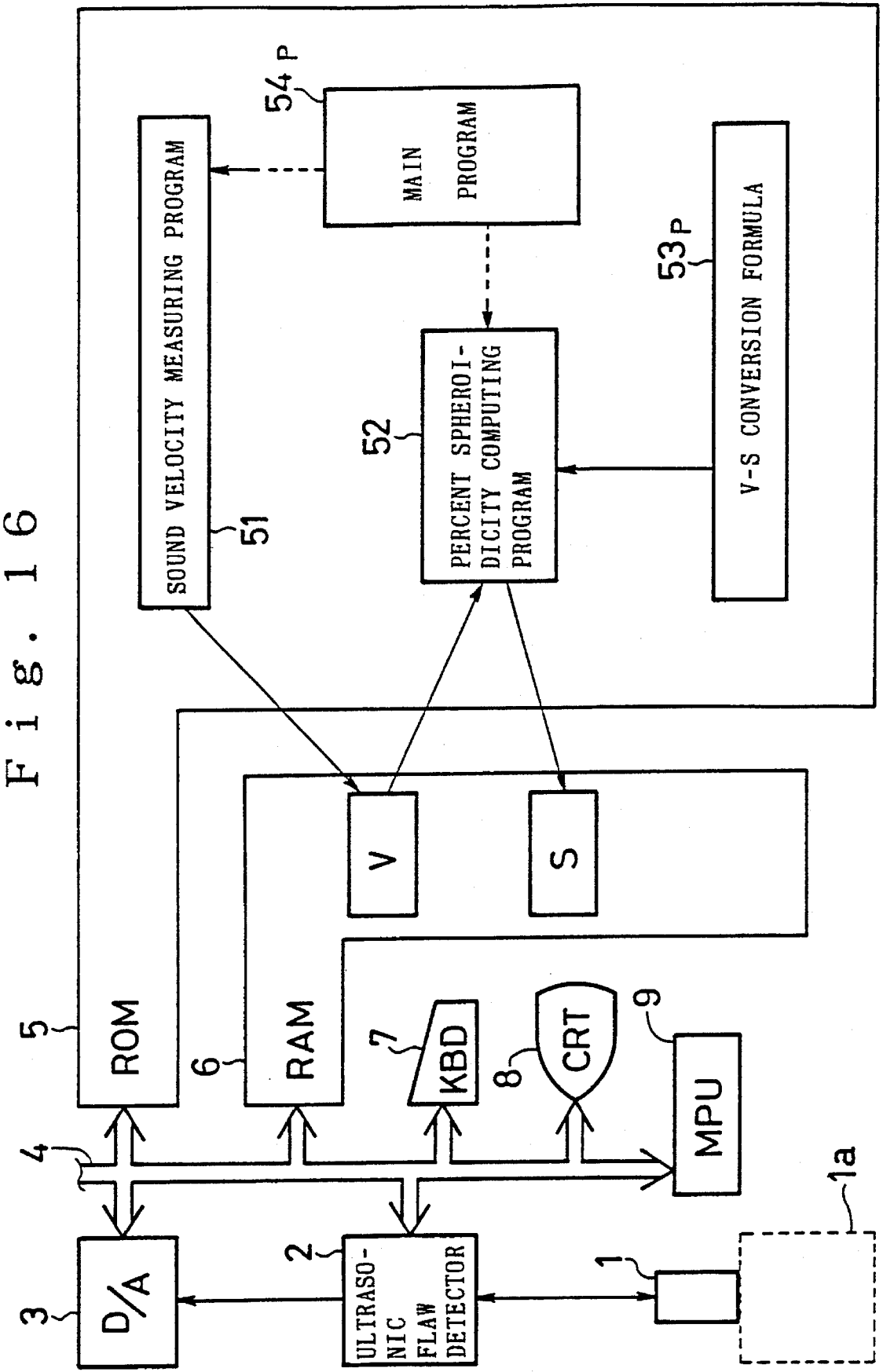
FIG. 16 is a block diagram of a conventional apparatus for measuring the percent spheroidicity of graphite.
Figure 17:
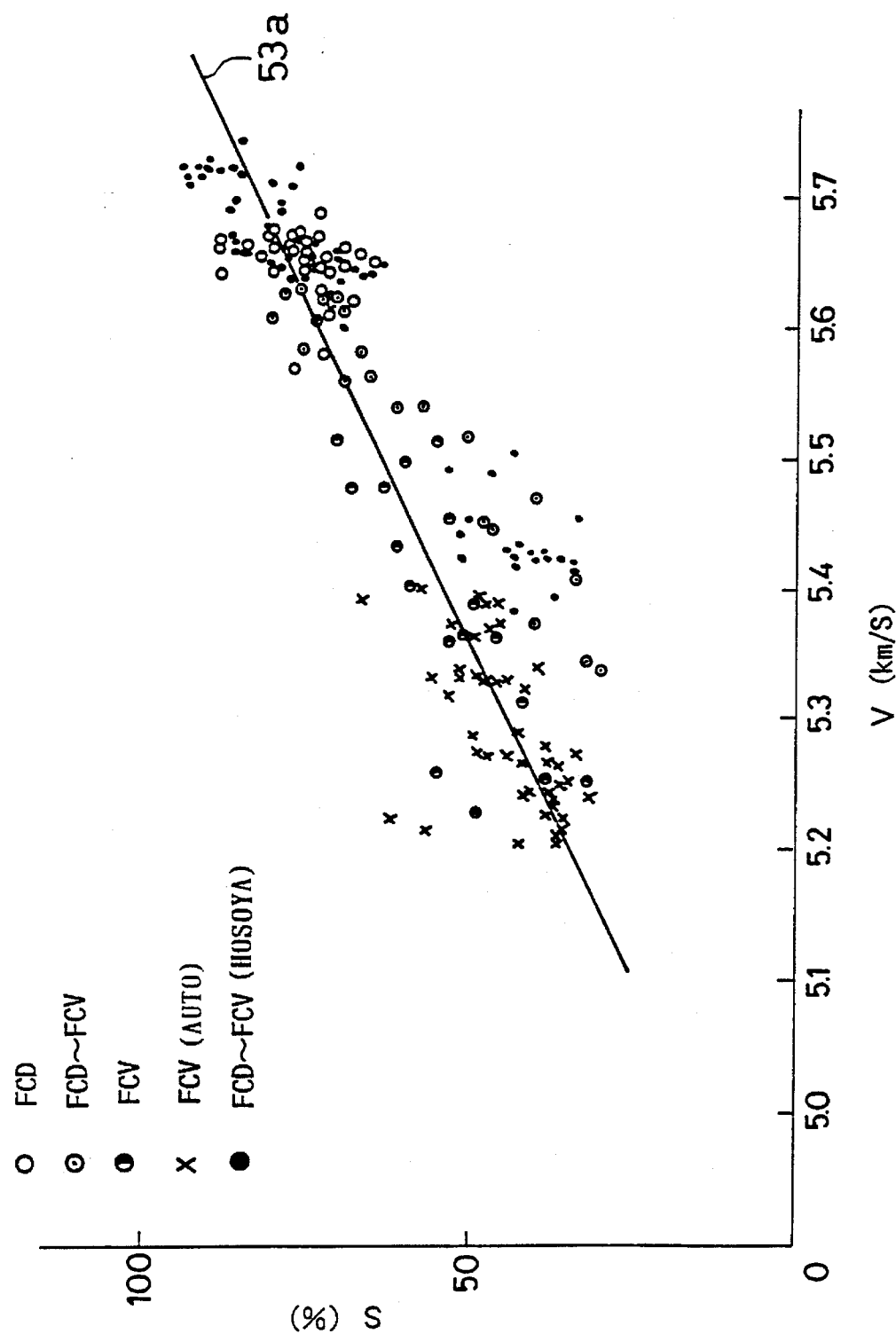
FIG. 17 is yet another example of the relationship between the sound velocity in castings and the percent spheroidicity of graphite.
Figure 19:
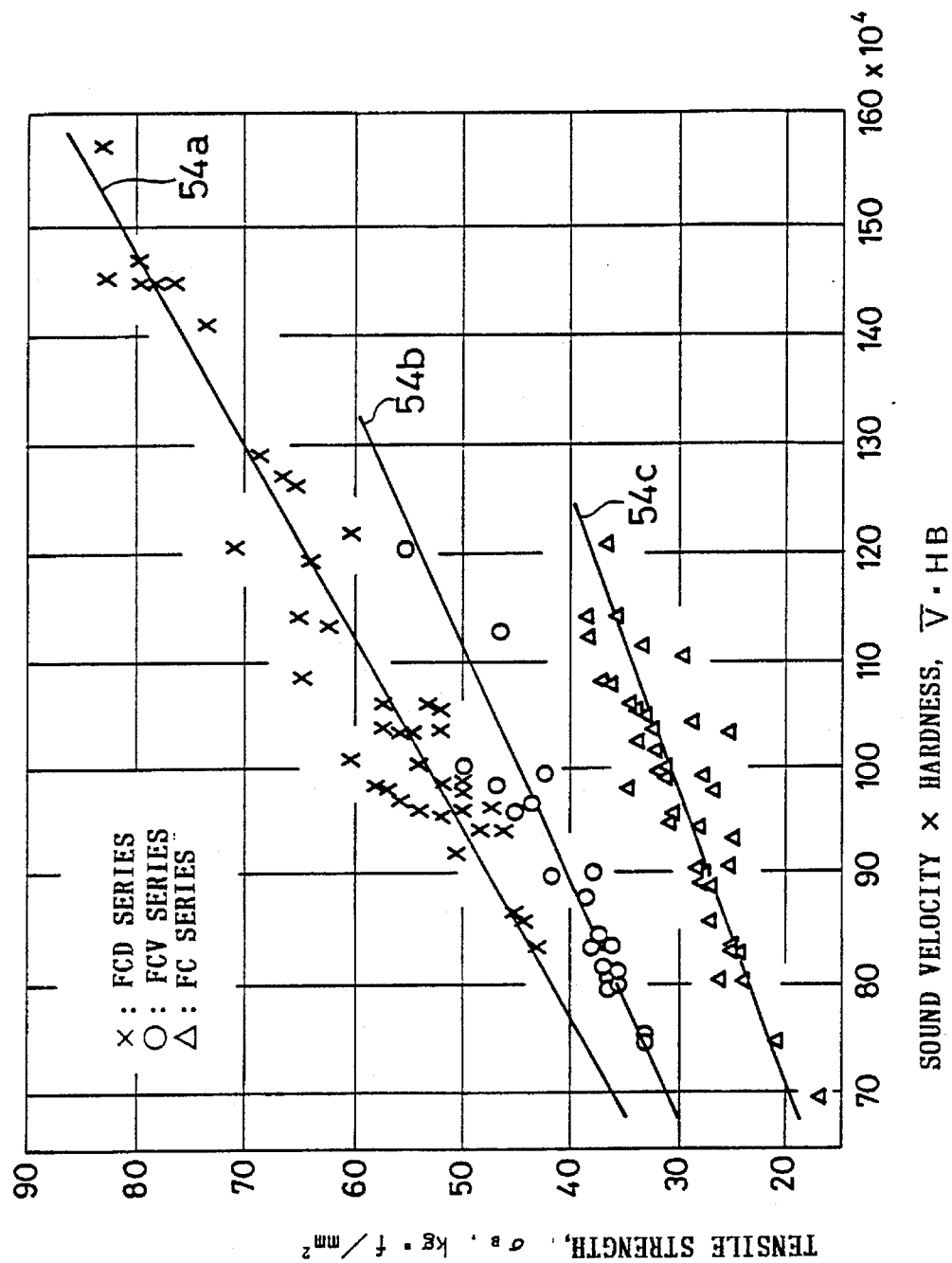
FIG. 19 shows in graphic form the correspondence between (sound velocity×hardness) and tensile strength.
Figure 20:
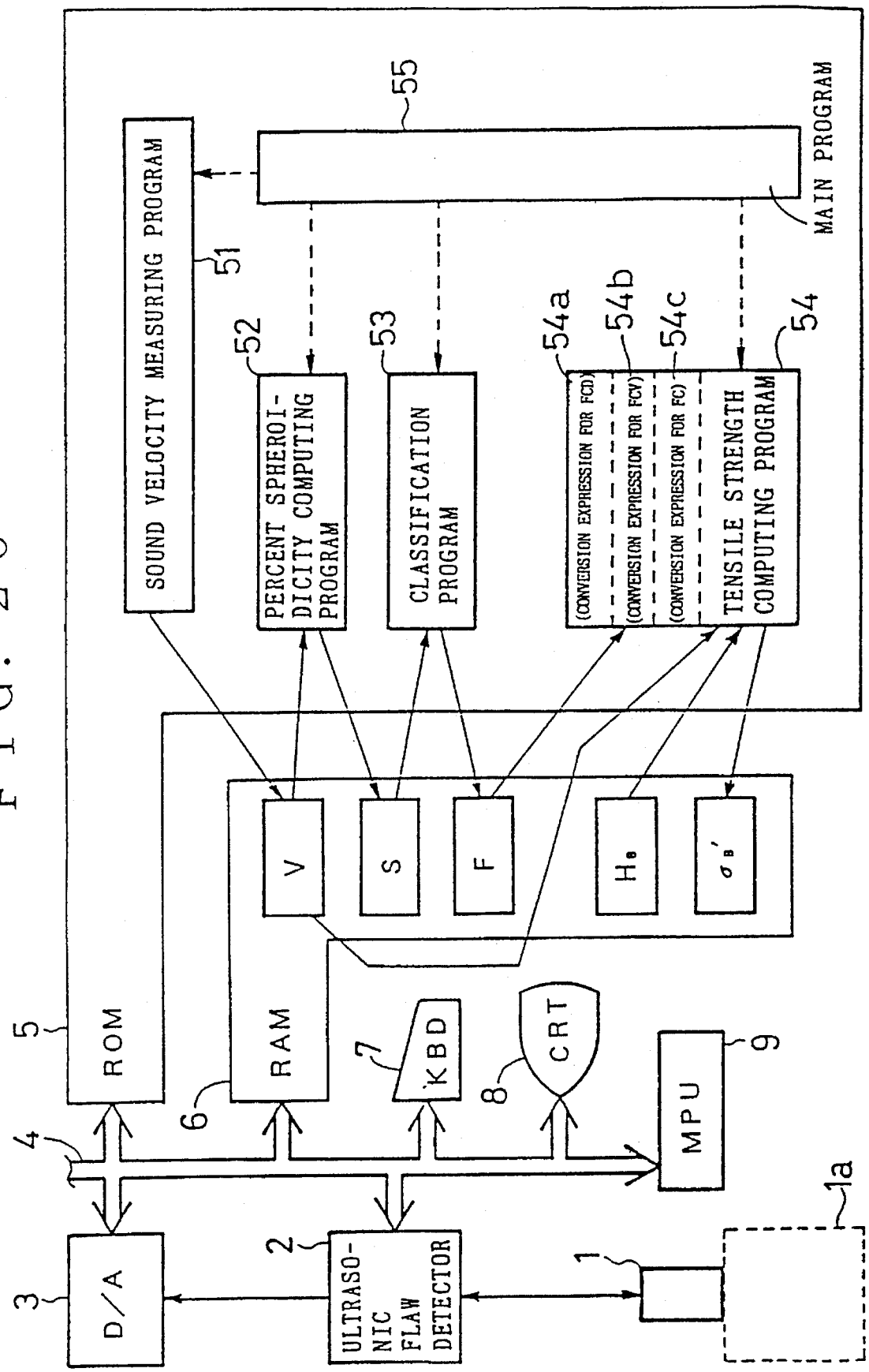
FIG. 20 is a block diagram of a conventional apparatus for measuring the tensile strength of castings.

The thusly computed percent elongation $\epsilon''$ provides a fairly good estimation of the actual percent elongation $\epsilon$ for the copper-containing cast iron (see FIG. 12).

With this configuration, the process of measuring the percent elongation of a cast product starts with measuring the sound velocity in a steel product in mode 1 (the mode for setting the sound velocity in steel), followed by processing cast products successively in mode 2 (the mode for measuring the percent elongation of castings).

Again, details of the process are substantially similar to the case of the already-described examples, and explanation of the overlapping portions will not be repeated. The only difference from the already-described examples is that, besides inputting the percent carbon content of the cast specimen 1a, its percent copper content (which is known as one of the data for the casting operation) is entered via keyboard 7 and set in area (Cu). If this data entry is omitted, processing is performed on the assumption that the percent copper content is the same as that of the previous specimen.

Thereafter, the percent elongation that has been computed by the percent elongation computing program 541 is stored in area $\epsilon''$ in RAM 6, and this percent elongation ($\epsilon''$) is displayed on CRT 8 by the main program 550 as the result of measurement and analysis.

This ensures the following and other facts to be detected in a simple and nondestructive manner: For example, heats that have been adjusted in components and the like by adding copper with a view to producing cast iron having high tensile strength turn out to be short of the intended percent elongation as a result of mismatch with processing or the like.

Thus, the percent elongation of castings can be measured or computed on a single cast product with high reliability in a nondestructive and easy manner, even if the cast product is copper-containing cast iron.

It should be noted that in all of the examples discussed hereinabove, the reference value for normalizing the sound velocity is desirably taken on a steel product that is in the same state as the so-called "casting matrix (base)"; however, other metals may be used as long as consistency is insured between the operation of preparing the computing procedures and that of actual measurements.

It should also be noted in the case of basing on the sound velocity rather than on the sound velocity ratio, namely, in the case where analyses or measurements are conducted on the basis of the percent carbon content, hardness, and sound velocity (or a combination of these with the percent copper content), the sound-velocity-in-steel setting program 511, the sound velocity normalizing program 512, etc. are unnecessary, and the above-described examples will apply as such if only the steel-related processing and the like are eliminated; hence, a detailed explanation of this alternative case is omitted.

Industrial Applicability

As described on the foregoing pages, the method and apparatus of the present invention for ultrasonic measurement are suitable for use on castings if one wants to determine reliable physical characteristic values (e.g. percent spheroidicity of graphite, tensile strength, and percent elongation) and state analysis values in a nondestructive and simple manner.

I claim:

1. In a method of ultrasonic measurement in which the velocity of propagation of an ultrasonic wave in a cast specimen is measured and a physical characteristic value of said specimen that has a physical correlation with said ultrasonic wave propagation velocity wave is determined, the improvement comprising the steps of:

determining a velocity ratio between the ultrasonic wave propagation velocity in said specimen and the velocity of ultrasonic wave propagation in a given metal that corresponds to said specimen; and converting the velocity ratio into the physical characteristic value, thereby determining said physical characteristic value of said specimen.

2. A method of ultrasonic measurement according to claim 1, wherein said converting step converts the velocity ratio into the physical characteristic value according to an empirical formula associated with the velocity ratio.

3. In an apparatus for ultrasonic measurement which measures the velocity of propagation of an ultrasonic wave in a cast specimen and determines a physical characteristic value of said cast specimen that has a physical correlation with said ultrasonic wave velocity of propagation, the improvement comprising:

processing means by which a first physical quantity is processed to determine a second physical quantity that is equivalent to said physical characteristic value of said cast specimen;

reference ultrasonic wave propagation velocity generating means by which the ultrasonic wave velocity of propagation as attained by ultrasonic measurement on a steel specimen is generated as a reference ultrasonic wave propagation velocity; and characteristic value generating means which determines said second physical quantity by said processing means and which generates the thus determined second physical quantity as said physical characteristic value of said cast specimen, the ratio between the ultrasonic wave propagation velocity in said cast specimen as attained by ultrasonic measurement on said specimen and said reference ultrasonic wave propagation velocity being an equivalent of said first physical quantity;

wherein the ultrasonic wave propagation velocity in the cast specimen and the ultrasonic wave propagation velocity in the steel specimen are both attained by measurement with the same apparatus for ultrasonic measurement, and wherein said processing means possesses either of a characteristic function or a table or a processing procedure that represents the correlation between said first physical quantity and said second physical quantity based on measurements of said ultrasonic wave propagation velocity in said cast specimen and of said physical characteristic value, which have been made previously on a plurality of samples of said cast specimen, said physical characteristic value having been measured directly on said cast specimen with a measuring apparatus other than the one for ultrasonic measurement.

4. An apparatus for ultrasonic measurement according to claim 3, wherein said processing means includes an empirical formula program.

5. In a method of ultrasonic measurement in which the velocity of propagation of an ultrasonic wave in a cast specimen is measured and the state of casting structure of said cast specimen that has a physical correlation with said ultrasonic wave propagation velocity is analyzed, the improvement comprising the steps of:

ascertaining the percent carbon content or carbon equivalent of said cast specimen and the velocity of propagation of ultrasonic wave in said specimen; and attaining an analytical value equivalent to said state of casting structure from the percent carbon content or carbon equivalent and ultrasonic wave propagation velocity in said cast specimen, whereby the state of casting structure in said cast specimen is analyzed in terms of said analytical value.

6. A method of ultrasonic measurement according to claim 5, wherein said attaining step attains the analytical value in accordance with an empirical formula.

7. In an apparatus for ultrasonic measurement which measures the velocity of propagation of an ultrasonic wave in a cast specimen with a known percent carbon content or carbon equivalent and analyzes the state of casting structure in said cast specimen, the improvement comprising:

processing means by which a first physical quantity and a second physical quantity are processed to determine a third physical quantity that is equivalent to said state of casting structure; and state evaluating means which determines said third physical quantity by said processing means, provided that the ultrasonic wave propagation velocity in said cast specimen as attained by ultrasonic measurement on said cast specimen is an equivalent of said first physical quantity, and that said percent carbon content or said carbon equivalent is an equivalent of said second physical quantity, said state evaluating means evaluating said state of casting structure in accordance with the thusly determined third physical quantity;

wherein said empirical formula program possesses either a characteristic function, a table or a processing procedure that represents the correlation between said first physical quantity, said second physical quantity, and said third physical quantity based on measurements of said ultrasonic wave propagation velocity in said cast specimen, of said percent carbon content or carbon equivalent and of said state of casting structure which have been measured previously on a plurality of samples of said cast specimen, said state of casting structure having been measured directly on said cast specimen with a measuring apparatus other than the one for ultrasonic measurement.

8. An apparatus for ultrasonic measurement according to claim 7, wherein said processing means includes an empirical formula program.

9. In an apparatus for ultrasonic measurement which measures the velocity of propagation of an ultrasonic wave in a cast specimen with a known percent carbon content or carbon equivalent and analyzes the state of casting structure in said cast specimen, the improvement comprising:

processing means by which a first physical quantity and a second physical quantity are processed to determine a third physical quantity that is equivalent to said state of casting structure;

reference ultrasonic wave propagation velocity generating means by which the ultrasonic wave propagation velocity as attained by ultrasonic measurement on a steel specimen is generated as a reference ultrasonic wave propagation velocity;

state evaluating means which determines said third physical quantity by said processing means, provided that the velocity ratio between the ultrasonic wave propagation velocity in said cast specimen as attained by ultrasonic measurement on said cast specimen and said reference ultrasonic wave propagation velocity is said first physical quantity, and that said percent carbon content or said carbon equivalent is an equivalent of said second physical quantity, said state evaluating means evaluating said state of casting structure in accordance with the thusly determined third physical quantity; and wherein said processing means possesses either a characteristic function, a table, or a processing procedure that represents the correlation between said first physical quantity, said second physical quantity, and said third physical quantity based on measurements of said ultrasonic wave propagation velocity, of said percent carbon content or said carbon equivalent, and said state of casting structure which have been measured previously on a plurality of samples of said cast specimen, said state of casting structure having been measured directly on said cast specimen with a measuring apparatus other than the one for ultrasonic measurement.

10. An apparatus for ultrasonic measurement according to claim 9, wherein said processing means includes an empirical formula program.

11. A method of ultrasonic measurement in which the velocity of propagation of an ultrasonic wave in a cast specimen is measured and the tensile strength of said cast specimen is determined, comprising the steps of:

attaining the percent content or carbon equivalent and the hardness of said specimen, as well as the ultrasonic wave propagation velocity in said cast specimen; and determining the tensile strength of said specimen from the percent carbon content or carbon equivalent, and from the hardness of said cast specimen and the ultrasonic wave propagation velocity in said cast specimen.

12. A method of ultrasonic measurement according to claim 11, wherein said determining step determines the tensile strength in accordance with an empirical formula, by which the tensile strength is attained from the percent carbon content or carbon equivalent, and from the hardness of the cast specimen and the ultrasonic wave propagation velocity in said cast specimen.

13. An apparatus for ultrasonic measurement which measures the velocity of propagation of an ultrasonic wave in a cast specimen with a known percent carbon content or carbon equivalent and determines the tensile strength of said cast specimen, comprising:

processing means by which a first physical quantity, a second physical quantity, and a third physical quantity are processed to determine a fourth physical quantity that is equivalent to said tensile strength; and tensile strength computing means which determines said fourth physical quantity by said processing means, provided that the ultrasonic wave propagation velocity in said cast specimen as attained by ultrasonic measurement on said cast specimen is an equivalent of said first physical quantity, said percent carbon content or carbon equivalent is an equivalent of said second physical quantity, and the hardness of said cast specimen is an equivalent of said third physical quantity, said tensile strength computing means outputting the thusly determined fourth physical quantity as the value of said tensile strength;

wherein said processing means possesses either a characteristic function, a table, or a processing procedure that represents the correlation between said first physical quantity, said second physical quantity, said third physical quantity, and said fourth physical quantity based on measurements of said ultrasonic wave propagation velocity, of said percent carbon content or carbon equivalent, of said hardness, and of said tensile strength which have been measured previously on a plurality of samples of said cast specimen, said tensile strength having been measured on said cast specimen by a direct means of tensile strength measurement other than the apparatus for ultrasonic measurement.

14. An apparatus for ultrasonic measurement according to claim 13, wherein said processing means includes an empirical formula program.

15. An apparatus for ultrasonic measurement which measures the velocity of propagation of an ultrasonic wave in a cast specimen with a known percent carbon content or carbon equivalent and determines the tensile strength of said cast specimen, comprising:

processing means by which a first physical quantity, a second physical quantity, and a third physical quantity are processed to determine a fourth physical quantity that is equivalent to said tensile strength;

reference ultrasonic wave propagation velocity generating means by which the ultrasonic wave propagation velocity as attained by ultrasonic measurement on a steel specimen is generated as a reference ultrasonic wave propagation velocity; and tensile strength computing means which determines said fourth physical quantity by said processing means, provided that the velocity ratio between the ultrasonic wave propagation velocity in said cast specimen as attained by ultrasonic measurement on said cast specimen and said reference ultrasonic wave propagation velocity is an equivalent of said first physical quantity, said percent carbon content or said carbon equivalent is an equivalent of said second physical quantity, and the hardness of said cast specimen is an equivalent of said third physical quantity, said tensile strength computing means outputting the thusly determined fourth physical quantity as the value of said tensile strength;

wherein said processing means possesses either a characteristic function, a table, or a processing procedure that represents the correlation between said first physical quantity, said second physical quantity, said third physical quantity, and said fourth physical quantity based on measurements of said ultrasonic wave propagation velocity, of said percent carbon content or carbon equivalent, of said hardness, and of said tensile strength which have been measured previously on a plurality of samples of said cast specimen, said tensile strength having been measured on said cast specimen by a direct means of tensile strength measurement other than the apparatus for ultrasonic measurement.

16. An apparatus for ultrasonic measurement according to claim 15, wherein said processing means includes an empirical formula program.

17. An apparatus for ultrasonic measurement which measures the velocity of propagation of an ultrasonic wave in a specimen of cast iron with a known percent carbon content or carbon equivalent and measures the tensile strength of said cast iron specimen, comprising:

tensile strength computing means for computing the equation $\rho=8.435-0.374\times C$; a second intermediate value fg by the equation $fg=1.095-0.1395\times\rho$; the equation $\alpha'=(R^{-2}\times(7.86/\rho)-1)/fg$; one of the empirical formulae $m'=0.3920-0.0512\times\alpha'$, $m'=0.2306$ and $m'=0.3000-0.0173\times\alpha'$ selectively under specified conditions; and the equation m'×H, wherein C is a first variable, R is a second variable, and H is a third variable; and reference ultrasonic wave propagation velocity setting means by which the ultrasonic wave propagation velocity in a steel specimen as attained by ultrasonic measurement on said steel specimen is outputted as a reference ultrasonic wave propagation velocity;

wherein said tensile strength computing means computes the tensile strength of said cast iron specimen by said equations, provided that the carbon percent content or carbon equivalent of said cast iron specimen is the value of said first variable C, that the velocity ratio between the ultrasonic wave propagation velocity in said cast iron specimen as attained by ultrasonic measurement on said cast iron specimen and said reference ultrasonic wave propagation velocity is the value of said second variable R, and that the hardness of said cast iron specimen is the value of said third variable H.

18. A method of ultrasonic measurement in which the velocity of propagation of an ultrasonic wave in a cast specimen is measured and the percent elongation of said cast specimen is determined, comprising the steps of:

determining the percent carbon content or carbon equivalent and the hardness of said cast specimen, as well as the ultrasonic wave propagation velocity in said cast specimen; and determining the percent elongation of said cast specimen from the percent carbon content or carbon equivalent and the hardness of said cast specimen and the ultrasonic wave propagation velocity in said cast specimen.

19. An method of ultrasonic measurement according to claim 18, wherein said step of determining the percent elongation is performed in accordance with an empirical formula, by which the percent elongation is attained from the percent carbon content or carbon equivalent, and the hardness of the cast specimen and the ultrasonic wave propagation velocity in said cast specimen.

20. An apparatus for ultrasonic measurement which measures the velocity of propagation of an ultrasonic wave in a cast specimen with a known percent carbon content or carbon equivalent and determines measures the percent elongation of said cast specimen, comprising:

processing means by which a first physical quantity, a second physical quantity, and a third physical quantity are processed to determine a fourth physical quantity that is equivalent to said percent elongation; and percent elongation computing means which determines said fourth physical quantity by said processing means, provided that the ultrasonic wave propagation velocity in said specimen as attained by ultrasonic measurement on said cast specimen is an equivalent of said first physical quantity, said percent carbon content or said carbon equivalent is an equivalent of said second physical quantity, and the hardness of said cast specimen is an equivalent of said third physical quantity, said percent elongation computing means outputting the thusly determined fourth physical quantity as the value of said percent elongation;

wherein said processing means possesses either a characteristic function, a table, or a processing procedure that represents the correlation between said first physical quantity, said second physical quantity, said third physical quantity, and said fourth physical quantity based on said ultrasonic wave propagation velocity, of said percent carbon content or carbon equivalent, of said hardness, and of said percent elongation which have been measured previously on a plurality of samples of said cast specimen, said percent elongation having been measured on said cast specimen by a direct means of percent elongation measurement other than the apparatus for ultrasonic measurement.

21. An apparatus for ultrasonic measurement according to claim 20, wherein said processing means includes an empirical formula program.

22. An apparatus for ultrasonic measurement which measures the velocity of propagation of an ultrasonic wave in a cast specimen with a known percent carbon content or carbon equivalent and determines the percent elongation of said cast specimen, comprising:

processing means by which a first physical quantity, a second physical quantity, and a third physical quantity are processed to determine a fourth physical quantity that is equivalent to said percent elongation;

reference ultrasonic wave propagation velocity generating means by which the ultrasonic wave propagation velocity as attained by ultrasonic measurement on a steel specimen is generated as a reference ultrasonic wave propagation velocity; and percent elongation computing means which determines said fourth physical quantity by said processing means, provided that the velocity ratio between the ultrasonic wave propagation velocity in said cast specimen as attained by ultrasonic measurement on said cast specimen and said reference ultrasonic wave propagation velocity is an equivalent of said first physical quantity, said percent carbon content or said carbon equivalent is an equivalent of said second physical quantity, and the hardness of said cast specimen is an equivalent of said third physical quantity, said percent elongation computing means outputting the thusly determined fourth physical quantity as the value of said percent elongation;

wherein said processing means possesses either a characteristic function, a table, or a processing procedure that represents the correlation between said first physical quantity, said second physical quantity, said third physical quantity, and said fourth physical quantity based on measurements of said ultrasonic wave propagation velocity, of said percent carbon content or carbon equivalent, of said hardness, and of said percent elongation which have been measured previously on a plurality of samples of said cast specimen, said percent elongation having been measured on said cast specimen by a direct means of percent elongation measurement other than the apparatus for ultrasonic measurement.

23. An apparatus for ultrasonic measurement according to claim 22, wherein said processing means includes an empirical formula program.

24. An apparatus for ultrasonic measurement which measures the velocity of propagation of an ultrasonic wave in a specimen of cast iron with a known percent carbon content or carbon equivalent, and determines the percent elongation of said cast iron specimen, comprising:

percent elongation computing means for computing the equation $\rho=8.435-0.374\times C$; the equation $fg=1.095-0.1395\times\rho$; the equation $\alpha'=(R^{-2}\times 7.86/\rho)-1)/fg$; one of the empirical formulae $m'=0.3920-0.0512\times\alpha'$, $m'=0.2306$, and $m'=0.3000-0.0173\times\alpha'$, which are applied selectively under specified conditions; the equation $m'\times H$; and one of $\epsilon'=3085-1035.6\times\alpha')/\sigma B'$ and $\epsilon'=(676.3-137.2\times\alpha')/\sigma B'$ which are applied selectively under specified conditions; wherein C is a first variable, R is a second variable, and H is a third variable; and reference ultrasonic wave propagation velocity setting means by which the ultrasonic wave propagation velocity in a steel specimen as attained by ultrasonic measurement on said steel specimen is outputted as a reference ultrasonic wave propagation velocity;

wherein said percent elongation computing means computes the percent elongation of said cast specimen by said equations, provided that the carbon content or carbon equivalent of said cast specimen is the value of said first variable C, that the velocity ratio between the ultrasonic wave propagation velocity in said cast specimen as attained by ultrasonic measurement on said cast specimen and said reference ultrasonic wave propagation velocity is the value of said second variable R, and that the hardness of said cast specimen is the value of said third variable H.

25. A method of ultrasonic measurement in which the velocity of propagation of an ultrasonic wave in a cast specimen is measured and the percent elongation of said cast specimen is determined, said cast specimen being a copper-containing cast iron, comprising the steps of:

attaining the percent copper content, the percent carbon content or carbon equivalent, and the hardness of said cast specimen, as well as the ultrasonic wave propagation velocity in said cast specimen; and determining the percent elongation of said cast specimen from the percent copper content, the percent carbon content or carbon equivalent, and the hardness of said cast specimen and the ultrasonic wave propagation velocity in said cast specimen.

26. A method of ultrasonic measurement according to claim 25, wherein said determining step determines the percent elongation in accordance with an empirical formula, by which the percent elongation is attained from the percent copper content, percent carbon content or carbon equivalent, and from the hardness of the cast specimen and the ultrasonic wave propagation velocity in said cast specimen.

27. An apparatus for ultrasonic measurement which measures the velocity of propagation of an ultrasonic wave in a specimen formed of a copper-contained cast iron with known percent copper and carbon content or carbon equivalent, and determines the percent elongation of said specimen, comprising:

processing means by which a first physical quantity, a second physical quantity, a third physical quantity, and a fourth physical quantity are processed to determine a fifth physical quantity that is equivalent to said percent elongation; and percent elongation computing means which determines said fifth physical quantity by said processing means, provided that the ultrasonic wave propagation velocity in said specimen as attained by ultrasonic measurement on said specimen is an equivalent of said first physical quantity, said percent carbon content or said carbon equivalent is an equivalent of said second physical quantity, the hardness of said specimen is an equivalent of said third physical quantity, and said percent copper content is an equivalent of said fourth physical quantity, said percent elongation computing means outputting the thusly determined fifth physical quantity as the value of said percent elongation;

wherein processing means possesses either a characteristic function, a table, or a processing procedure that represents the correlation between said first physical quantity, said second physical quantity, said third physical quantity, said fourth physical quantity, and said fifth physical quantity based on measurements of said ultrasonic wave propagation velocity, of said hardness, of said percent carbon content or carbon equivalent, of said percent copper content, and of said percent elongation which have been measured previously on a plurality of samples of said specimen, said percent elongation having been previously measured on said specimen by a direct means of percent elongation measurement other than the apparatus for ultrasonic measurement.

28. An apparatus for ultrasonic measurement according to claim 27, wherein said processing means includes an empirical formula program.

29. An apparatus for ultrasonic measurement which measures the velocity of propagation of an ultrasonic wave in a copper-containing cast iron specimen with known percent copper and carbon content or carbon equivalent, and determines the percent elongation of said copper-containing cast iron specimen, comprising:

processing means by which a first physical quantity, a second physical quantity, a third physical quantity, and a fourth physical quantity are processed to determine a fifth physical quantity that is equivalent to said percent elongation;

reference ultrasonic wave propagation velocity generating means by which the ultrasonic wave propagation velocity as attained by ultrasonic measurement on a steel specimen is generated as a reference ultrasonic wave propagation velocity; and percent elongation computing means which determines said fifth physical quantity by said processing means, provided that the velocity ratio between the ultrasonic wave propagation velocity in said copper-containing cast iron specimen as attained by ultrasonic measurement on said specimen and said reference ultrasonic wave propagation velocity is an equivalent of said first physical quantity, said percent carbon content or said carbon equivalent is an equivalent of said second physical quantity, the hardness of said copper-containing cast iron specimen is an equivalent of said third physical quantity, and said percent copper content is an equivalent of said fourth physical quantity, said percent elongation computing means outputting the thusly determined fifth physical quantity as the value of said percent elongation;

wherein said processing means possesses either a characteristic function, a table, or a processing procedure that represents the correlation between said first physical quantity, said second physical quantity, said third physical quantity, said fourth physical quantity, and said fifth physical quantity based on measurements of said ultrasonic wave propagation velocity, of said percent carbon content or carbon equivalent, of said hardness, of said percent copper content, and of said percent elongation which have been measured previously on a plurality of samples of said copper-containing cast iron specimen, said percent elongation having been measured on said copper-containing cast iron specimen by a direct means of percent elongation measurement other than the apparatus for ultrasonic measurement.

30. An apparatus for ultrasonic measurement according to claim 29, wherein said processing means includes an empirical formula program.

31. An apparatus for ultrasonic measurement which measures the velocity of propagation of an ultrasonic wave in a specimen of copper-containing cast iron with known percent copper and carbon content or carbon equivalent, and determines the percent elongation of said copper-containing cast iron specimen, comprising:

percent elongation computing means for computing the equation $\rho=8.435-0.374\times C$; the equation $fg=1.095-0.1395\times\rho$; the equation $\alpha'=(R^{-2}\times(7.86/\rho)-1)/fg$; one of the empirical formulae $m'=0.3920-0.0512\times\alpha'$, $m'=0.2306$, and $m'-0.3000-0.0173\times\alpha'$ which are applied selectively under specified conditions; the equation $m'\times H$; and any one of empirical formulae $\epsilon''=(0.165\times(3085-1035.6\times\alpha')/(\sigma B' \times Cu))+2.3$ and $\epsilon''=(0.165\times 676.3-137.2\times\alpha')/(\sigma B'\times Cu))+2.3$ which are applied selectively under specified conditions; wherein C is a first variable, R is a second variable, H is a third variable, and Cu is a fourth variable; and reference ultrasonic wave propagation velocity setting means by which the velocity of propagation of an ultrasonic wave in a steel specimen as attained by ultrasonic measurement on said steel specimen is outputted as a reference ultrasonic wave propagation velocity;

wherein said percent elongation computing means computes the percent elongation of said copper-containing cast iron specimen by said equations, provided that the carbon content or carbon equivalent of said copper-containing cast iron specimen is the value of said first variable C, that the velocity ratio between the ultrasonic wave propagation velocity in said copper-containing cast iron specimen as attained by ultrasonic measurement on said copper-containing cast iron specimen and said reference ultrasonic wave propagation velocity is the value of said second variable R, that the hardness of said copper-containing cast iron specimen is the value of said third variable H, and that the percent copper content of said copper-containing cast iron specimen is the value of said fourth variable Cu.

* * * * *